US008623369B2

(12) United States Patent
Abulrob et al.

(10) Patent No.: US 8,623,369 B2
(45) Date of Patent: Jan. 7, 2014

(54) ANTI-ICAM-1 SINGLE DOMAIN ANTIBODY AND USES THEREOF

(75) Inventors: Abedelnasser Abulrob, Orleans (CA); Mehdi Arbabi-Ghahroudi, Ottawa (CA); Danica Stanimirovic, Greely (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

(21) Appl. No.: 13/643,412

(22) PCT Filed: Apr. 27, 2011

(86) PCT No.: PCT/CA2011/000481
§ 371 (c)(1),
(2), (4) Date: Oct. 25, 2012

(87) PCT Pub. No.: WO2011/134060
PCT Pub. Date: Nov. 3, 2011

(65) Prior Publication Data
US 2013/0064763 A1    Mar. 14, 2013

Related U.S. Application Data

(60) Provisional application No. 61/328,406, filed on Apr. 27, 2010.

(51) Int. Cl.
*A61K 39/395*    (2006.01)
*C07K 16/28*    (2006.01)
*G01N 33/53*    (2006.01)

(52) U.S. Cl.
USPC ... 424/152.1; 424/9.1; 424/130.1; 424/133.1; 424/141.1; 424/143.1; 424/172.1; 530/387.1; 530/387.3; 530/388.2; 530/388.22; 435/7.1; 435/7.2; 435/7.21

(58) Field of Classification Search
None
See application file for complete search history.

(56) References Cited

FOREIGN PATENT DOCUMENTS

WO    03/46560 A2    6/2003
WO    2008/147526 A1    12/2008

OTHER PUBLICATIONS

Arbabi Ghahroudi M, Desmyter A, Wyns L, Hamers R, Muyldermans S.Selection and identification of single domain antibody fragments from camel heavy-chain antibodies. FEBS Lett. 1997;414:521-6.
Arbabi-Ghahroudi M, MacKenzie R, Tanha J. Selection of non-aggregating VH binders from synthetic VH phage-display libraries. Methods Mol Biol. 2009;525:187-216, xiii.
Bell A, Wang ZJ, Arbabi-Ghahroudi M, Chang TA, Durocher Y, Trojahn U, Baardsnes J, Jaramillo ML, Li S, Baral TN, O'Connor-McCourt M, Mackenzie R, Zhang J. Differential tumor-targeting abilities of three single-domain antibody formats. Cancer Lett. 2010;289:81-90.
Chothia C, Lesk AM. Canonical structures for the hypervariable regions of immunoglobulins. J Mol Biol. 1987;196 (4):901-17.
de Kruif, J. & Logtenberg, T. Leucine zipper dimerized bivalent and bispecific scFv antibodies from a semi-synthetic antibody phage display library. J Biol Chem 271, 7630-7634 (1996).
Danila, D. et al (2009) Antibody-Labeled Liposomes for CT Imaging of Atherosclerotic Plaques. Texas Heart Institute Journal. p. 393-403.
Dougherty G.J., Murdoch S., and Hogg N. The function of human intercellular adhesion molecule- 1 (ICAM-I) in the generation of an immune response. Eur J Immunol 1988:18, 35-39.
Doyle PJ, Arbabi-Ghahroudi M, Gaudette N, Furzer G, Savard ME, Gleddie S, McLean MD, Mackenzie CR, Hall JC. Cloning, expression, and characterization of a single-domain antibody fragment with affinity for 15-acetyl-deoxynivalenol. Mol Immunol. 2008;45:3703-13.
Eisenberg, D.; E. Schwarz; M. Komaromy & R. Wall (1984) Analysis of membrane and surface protein sequences with the hydrophobic moment plot. J Mol Biol, 179, 125-142.
Hamers-Casterman, C. et al. Naturally occurring antibodies devoid of light chains. Nature 363, 446-448 (1993).
Iiyama K, Hajra L, Iiyama M, Li H, DiChiara M, Medoff BD, Cybulsky MI (1999), Patterns of vascular cell adhesion molecule-1 and intercellular adhesion molecule-1 expression in rabbit and mouse atherosclerotic lesions and at sites predisposed to lesion formation. Circ Res 1999:85:199-207.
Iqbal U, Trojahn U, Albaghdadi H, Zhang J, O'Connor M, Stanimirovic D, Tomanek B, Sutherland G, Abulrob A (2010) Kinetic analysis of novel mono- and multivalent VHH-fragments and their application for molecular targeting of brain tumors. British Journal of Pharmacology (in press).
Jaff MR, Goldmakher GV, Lev MH, Romero JM. Imaging of the carotid arteries: the role of duplex ultrasonography, magnetic resonance arteriography, and computerized tomographic arteriography. Vasc Med. Nov. 2008;13(4):281-92.
Jespers, L., Schon, O., Famm, K. & Winter, G. Aggregation-resistant domain antibodies selected on phage by heat denaturation. Nat Biotechnol 22, 1161-1165 (2004).
Kabat EA, Wu TT. Identical V region amino acid sequences and segments of sequences in antibodies of different specificities. Relative contributions of VH and VL genes, minigenes, and complementarity-determining regions to binding of antibody-combining sites. J Immunol. 1991;147:1709-19.
Kitagawa K, Matsumoto M, Sasaki T, Hashimoto H, Kuwabara K, Ohtsuki T, Hori M (2002), Involvement of ICAM-1 in the progression of atherosclerosis in APOE-knockout mice, Atherosclerosis 160: 305-310.

(Continued)

*Primary Examiner* — Phillip Gambel
(74) *Attorney, Agent, or Firm* — Sonia Patenaude

(57) ABSTRACT

Anti-ICAM-1 $V_HH$ single-domain antibodies (sdAbs) are generated by immunizing a llama with recombinant ICAM-1. These antibodies are linked to an imaging moiety for in vivo or ex vivo imaging of ICAM-1-related pathological conditions including atherosclerotic plaques. The antibodies may also be linked to a therapeutic agent to specifically target and treat ICAM-1-related pathological conditions.

19 Claims, 24 Drawing Sheets

(56) References Cited

OTHER PUBLICATIONS

Merritt, E.A. & Hol, W.G. AB5 toxins. Current opinion in structural biology 5, 165-171 (1995).

Nakashima Y, Raines EW, Plump AS, Breslow JL, Ross R. Upregulation of VCAM-1 and ICAM-1 at atherosclerosis-prone sites on the endothelium in the ApoE-deficient mouse. Arterioscler Thromb Vasc Biol. 1998:18:842-51.

Nielsen, U.B., Adams, G.P., Weiner, L.M. & Marks, J.D. Targeting of bivalent anti-ErbB2 diabody antibody fragments to tumor cells is independent of the intrinsic antibody affinity. Cancer research 60, 6434-6440 (2000).

Nuttall, S.D. et al. Isolation and characterization of an IgNAR variable domain specific for the human mitochondrial translocase receptor Tom70. European journal of biochemistry / FEBS 270, 3543-3554 (2003).

Padlan, E.A. Anatomy of the antibody molecule. Molecular immunology 31, 169-217 (1994).

Ridgway, J.B., Presta, L.G. & Carter, P. 'Knobs-into-holes' engineering of antibody CH3 domains for heavy chain heterodimerization. Protein Eng 9, 617-621 (1996).

Sadat U, Li ZY, Graves MJ, Tang TY, Gillard JH. Noninvasive imaging of atheromatous carotid plaques. Nat Clin Pract Cardiovasc Med. Mar. 2009;6(3):200-9.

Tanha J, Muruganandam A, Stanimirovic D. Phage display technology for identifying specific antigens on brain endothelial cells. Methods Mol Med. 2003;89:435-49.

Tanha J, Xu P, Chen Z, Ni F, Kaplan H, Narang SA, MacKenzie CR. Optimal design features of camelized human single-domain antibody libraries. J Biol Chem. Jul. 6, 2001;276(27):24774-80.

To, R. et al. Isolation of monomeric human V(H)s by a phage selection. J Biol Chem 280, 41395-41403 (2005).

Zhang, J. et al. A pentavalent single-domain antibody approach to tumor antigen discovery and the development of novel proteomics reagents. J Mol Biol 341, 161-169 (2004).

Zhang, J. et al. Pentamerization of single-domain antibodies from phage libraries: a novel strategy for the rapid generation of high-avidity antibody reagents. J Mol Biol 335, 49-56 (2004).

PCT/CA2011/000481 International Search Report, Apr. 27, 2011.

PCT/CA2011/000481 Written Opinion, Apr. 27, 2011.

PCT/CA2011/000481 International Preliminary Report on Patentability, Apr. 27, 2011.

11774229.6 EPO Communication Nov. 8, 2012.

CAGGTGCAGCTGGTGGAGTCTGGGGGAGGCTTGGTGCAGCCTGGGGGGTC
TCTGAGACTCTCCTGCGCAGCCTCTGGAAGCATCTCCAGTCTGTATGTCATG
GGCTGGTACCGCCAGGCTCCAGGGAAGCAGCGCGAGTTGGTCGCAGATATT
ACTAGTAGTGGTAGCATATACTATGTAGACTCCTTGAAGGGCCGATTCACCAT
CTCCAGAGACAACGCCAGGAGCACGGTGTATCTGCAAATGAACAGCCTAGAA
CCTGAGGACACGGCTGTGTATTACTGTATGGCACACGTGAGGCAAGATAGTG
GTAGTGAGTACCTCACCTACTGGGGCCAGGGGACCCAGGTCACCGTCTCCT
CAGGATCCGAACAAAAACTGATCAGCGAAGAAGATCTGAACCATCACCATCA
CCAT    SEQ ID NO:13

QVQLVESGGGLVQPGGSLRLSCAASGSISSLYVMGWYRQAPGKQRELVADITSS
GSIYYVDSLKGRFTISRDNARSTVYLQMNSLEPEDTAVYYCMAHVRQDSGSEYL
TYWGQGTQVTVSSGS<u>EQKLISEEDL</u>NHHHHH SEQ ID NO:14

FIG. 2

CAGGTAAAGCTGGAGGAGTCTGGGGGAGGATTGGTGCAGGCTGGGGACTCT
CTGAGACTCTCCTGTGCAGCCTCTGGACGCACCGTCAATGCCTTTCGCATGG
GCTGGTACCGCCAGGCTCCAGGAAAGCAGCGCGAGCGGGTCGCTGTTATCA
CTGCTGGTGGTACCACATCCTATATAGACTCCGTGAAGGGCCGATTCACCAT
CTCCAGAGACAACGCCAAGAACACGGTCTATCTGCAAATGAACAGCCTGAAA
CCTGAGGATACGGCCGTCTATTACTGTGCAGCGATTGACTATGACAGCCGGG
GCCAGGGGACCCAGGTCACCGTCTCCTCAGGATCCGAACAAAAACTGATCAG
CGAAGAAGATCTGAACCATCACCATCACCAT        SEQ ID NO:15

QVKLEESGGGLVQAGDSLRLSCAASGRTVNAFRMGWYRQAPGKQRERVAVITA
GGTTSYIDSVKGRFTISRDNAKNTVYLQMNSLKPEDTAVYYCAAIDYDSRGQGTQ
VTVSSGS<u>EQKLISEEDL</u>NHHHHH        SEQ ID NO:16

FIG. 3

CAGGTAAAGCTGGAGGAGTCTGGGGGAGGCTTGGTGCAGCCTGGGGGGTCT
CTGAGGCTCTCCTGTGCAGCCTCTGGAAGCATCTTCAGTATCAATGACATGG
GCTGGTACCGCCAGGCTCCGGGGAAGCAGCGCGAGTTGGTCGCACGTATTA
CTCGTGACGGTAGTGCTGCCTATGAAGACTCCGTGAAGGGCCGATTCACCAT
CTCCAGAGACAACGCCCCGAACACGGTATTTCTGCAAATGAACGGCCTGAAA
CCTGAGGACACGGCCGTCTATTACTGTAATGCAGAGATTATTACTACTCAGAC
TCTGGGTCGCATGCTGGGGGAGTATTGGGGACAGGGGACCCAGGTCACCGT
CTCCTCAGGCCAGGCCGGCCAGGGATCCGAACAAAAACTGATCAGCGAAGA
AGATCTGAACCATCACCATCACCATCAC        SEQ ID NO:17

QVKLEESGGGLVQPGGSLRLSCAASGSIFSINDMGWYRQAPGKQRELVARITRD
GSAAYEDSVKGRFTISRDNAPNTVFLQMNGLKPEDTAVYYCNAEIITTQTLGRML
GEYWGQGTQVTVSSGQAGQGS<u>EQKLISEEDL</u>NHHHHH    SEQ ID NO:18

FIG. 4

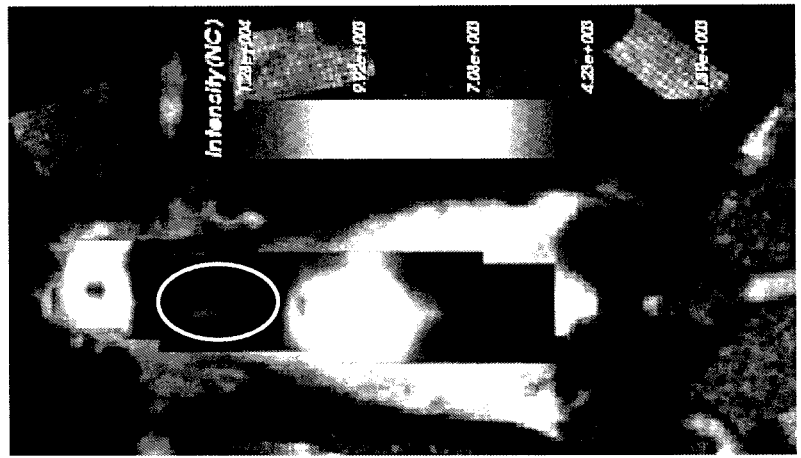
FIG. 16

3hr    5hr    6hr

SEQUENCE LISTING

<160> NUMBER OF SEQ ID NOS: 25

<210> SEQ ID NO 1
<211> LENGTH: 5
<212> TYPE: PRT
<213> ORGANISM: lama glama

<400> SEQUENCE: 1

Leu Tyr Val Met Gly
1               5

<210> SEQ ID NO 2
<211> LENGTH: 5
<212> TYPE: PRT
<213> ORGANISM: lama glama

<400> SEQUENCE: 2

Ala Phe Arg Met Gly
1               5

<210> SEQ ID NO 3
<211> LENGTH: 5
<212> TYPE: PRT
<213> ORGANISM: lama glama

<400> SEQUENCE: 3

Ile Asn Asp Met Gly
1               5

<210> SEQ ID NO 4
<211> LENGTH: 16
<212> TYPE: PRT
<213> ORGANISM: lama glama

<400> SEQUENCE: 4

Asp Ile Thr Ser Ser Gly Ser Ile Tyr Tyr Val Asp Ser Leu Lys Gly
1               5                   10                  15

<210> SEQ ID NO 5
<211> LENGTH: 16
<212> TYPE: PRT
<213> ORGANISM: lama glama

<400> SEQUENCE: 5

Val Ile Thr Ala Gly Gly Thr Thr Ser Tyr Ile Asp Ser Val Lys Gly
1               5                   10                  15

<210> SEQ ID NO 6
<211> LENGTH: 16
<212> TYPE: PRT
<213> ORGANISM: lama glama

<400> SEQUENCE: 6

Arg Ile Thr Arg Asp Gly Ser Ala Ala Tyr Glu Asp Ser Val Lys Gly
1               5                   10                  15

<210> SEQ ID NO 7
<211> LENGTH: 13
<212> TYPE: PRT
<213> ORGANISM: lama glama

<400> SEQUENCE: 7

His Val Arg Gln Asp Ser Gly Ser Glu Tyr Leu Thr Tyr
1               5                   10

<210> SEQ ID NO 8
<211> LENGTH: 5
<212> TYPE: PRT
<213> ORGANISM: lama glama

<400> SEQUENCE: 8

Ile Asp Tyr Asp Ser
1               5

<210> SEQ ID NO 9
<211> LENGTH: 15
<212> TYPE: PRT
<213> ORGANISM: lama glama

<400> SEQUENCE: 9

Glu Ile Ile Thr Thr Gln Thr Leu Gly Arg Met Leu Gly Glu Tyr
1               5                   10                  15

<210> SEQ ID NO 10
<211> LENGTH: 121
<212> TYPE: PRT
<213> ORGANISM: lama glama

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Ser Leu Tyr
            20                  25                  30

Val Met Gly Trp Tyr Arg Gln Ala Pro Gly Lys Gln Arg Glu Leu Val
        35                  40                  45

Ala Asp Ile Thr Ser Ser Gly Ser Ile Tyr Tyr Val Asp Ser Leu Lys
    50                  55                  60

Gly Arg Phe Thr Ile Ser Arg Asp Asn Ala Arg Ser Thr Val Tyr Leu
65                  70                  75                  80

Gln Met Asn Ser Leu Glu Pro Glu Asp Thr Ala Val Tyr Tyr Cys Met
                85                  90                  95

Ala His Val Arg Gln Asp Ser Gly Ser Glu Tyr Leu Thr Tyr Trp Gly
            100                 105                 110

Gln Gly Thr Gln Val Thr Val Ser Ser
        115                 120

<210> SEQ ID NO 11
<211> LENGTH: 113
<212> TYPE: PRT
<213> ORGANISM: lama glama

<400> SEQUENCE: 11

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Thr Val Asn Ala Phe
            20                  25                  30

Arg Met Gly Trp Tyr Arg Gln Ala Pro Gly Lys Gln Arg Glu Arg Val
        35                  40                  45

Ala Val Ile Thr Ala Gly Gly Thr Thr Ser Tyr Ile Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ile Asp Tyr Asp Ser Arg Gly Gln Gly Thr Gln Val Thr Val Ser
                100                 105                 110

Ser

<210> SEQ ID NO 12
<211> LENGTH: 123
<212> TYPE: PRT
<213> ORGANISM: lama glama

<400> SEQUENCE: 12

Gln Val Lys Leu Glu Glu Ser Gly Gly Leu Val Gln Pro Gly Gly
1               5                   10                  15

Ser Leu Arg Leu Ser Cys Ala Ala Ser Gly Ser Ile Phe Ser Ile Asn
                20                  25                  30

Asp Met Gly Trp Tyr Arg Gln Ala Pro Gly Lys Gln Arg Glu Leu Val
            35                  40                  45

Ala Arg Ile Thr Arg Asp Gly Ser Ala Ala Tyr Glu Asp Ser Val Lys
        50                  55                  60

Gly Arg Phe Thr Ile Ser Arg Asp Asn Ala Pro Asn Thr Val Phe Leu
65              70                  75                  80

Gln Met Asn Gly Leu Lys Pro Glu Asp Thr Ala Val Tyr Tyr Cys Asn
                85                  90                  95

Ala Glu Ile Ile Thr Thr Gln Thr Leu Gly Arg Met Leu Gly Glu Tyr
                100                 105                 110

Trp Gly Gln Gly Thr Gln Val Thr Val Ser Ser
            115                 120

<210> SEQ ID NO 13
<211> LENGTH: 417
<212> TYPE: DNA
<213> ORGANISM: Artificial Sequence
<220> FEATURE:
<223> OTHER INFORMATION: SdAb 11-4

<400> SEQUENCE: 13
caggtgcagc tggtggagtc tgggggaggc ttggtgcagc ctggggggtc tctgagactc      60
tcctgcgcag cctctggaag catctccagt ctgtatgtca tgggctggta ccgccaggct     120
ccagggaagc agcgcgagtt ggtcgcagat attactagta gtggtagcat atactatgta     180
gactccttga agggccgatt caccatctcc agagacaacg ccaggagcac ggtgtatctg     240
caaatgaaca gcctagaacc tgaggacacg gctgtgtatt actgtatggc acacgtgagg     300
caagatagtg gtagtgagta cctcacctac tggggccagg ggacccaggt caccgtctcc     360
tcaggatccg aacaaaaact gatcagcgaa gaagatctga accatcacca tcaccat       417

<210> SEQ ID NO 14
<211> LENGTH: 139
<212> TYPE: PRT
<213> ORGANISM: Artificial Sequence
<220> FEATURE:
<223> OTHER INFORMATION: sdAb 11-4

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Ser Leu Tyr
                20                  25                  30

Val Met Gly Trp Tyr Arg Gln Ala Pro Gly Lys Gln Arg Glu Leu Val
            35                  40                  45

```
Ala Asp Ile Thr Ser Ser Gly Ser Ile Tyr Tyr Val Asp Ser Leu Lys
        50                  55                  60
Gly Arg Phe Thr Ile Ser Arg Asp Asn Ala Arg Ser Thr Val Tyr Leu
 65                  70                  75                  80
Gln Met Asn Ser Leu Glu Pro Glu Asp Thr Ala Val Tyr Tyr Cys Met
                85                  90                  95
Ala His Val Arg Gln Asp Ser Gly Ser Glu Tyr Leu Thr Tyr Trp Gly
               100                 105                 110
Gln Gly Thr Gln Val Thr Val Ser Ser Gly Ser Glu Gln Lys Leu Ile
            115                 120                 125
Ser Glu Glu Asp Leu Asn His His His His
        130                 135
```

```
<210> SEQ ID NO 15
<211> LENGTH: 393
<212> TYPE: DNA
<213> ORGANISM: Artificial Sequence
<220> FEATURE:
<223> OTHER INFORMATION: sdAb 5-5

<400> SEQUENCE: 15
caggtaaagc tggaggagtc tgggggagga ttggtgcagg ctggggactc tctgagactc      60
tcctgtgcag cctctggacg caccgtcaat gcctttcgca tgggctggta ccgccaggct     120
ccaggaaagc agcgcgagcg ggtcgctgtt atcactgctg gtggtaccac atcctatata     180
gactccgtga agggccgatt caccatctcc agagacaacg ccaagaacac ggtctatctg     240
caaatgaaca gcctgaaacc tgaggatacg gccgtctatt actgtgcagc gattgactat     300
gacagccggg gccaggggac ccaggtcacc gtctcctcag gatccgaaca aaaactgatc     360
agcgaagaag atctgaacca tcaccatcac cat                                   393
```

```
<210> SEQ ID NO 16
<211> LENGTH: 131
<212> TYPE: PRT
<213> ORGANISM: Artificial Sequence
<220> FEATURE:
<223> OTHER INFORMATION: sdAb 5-5

<400> SEQUENCE: 16

Gln Val Lys Leu Glu Glu Ser Gly Gly Gly Leu Val Gln Ala Gly Asp
 1               5                  10                  15
Ser Leu Arg Leu Ser Cys Ala Ala Ser Gly Arg Thr Val Asn Ala Phe
            20                  25                  30
Arg Met Gly Trp Tyr Arg Gln Ala Pro Gly Lys Gln Arg Glu Arg Val
         35                  40                  45
Ala Val Ile Thr Ala Gly Gly Thr Thr Ser Tyr Ile Asp Ser Val Lys
     50                  55                  60
Gly Arg Phe Thr Ile Ser Arg Asp Asn Ala Lys Asn Thr Val Tyr Leu
 65                  70                  75                  80
Gln Met Asn Ser Leu Lys Pro Glu Asp Thr Ala Val Tyr Tyr Cys Ala
                85                  90                  95
Ala Ile Asp Tyr Asp Ser Arg Gly Gln Gly Thr Gln Val Thr Val Ser
               100                 105                 110
Ser Gly Ser Glu Gln Lys Leu Ile Ser Glu Glu Asp Leu Asn His His
            115                 120                 125
His His His
        130
```

<210> SEQ ID NO 17
<211> LENGTH: 441
<212> TYPE: DNA
<213> ORGANISM: Artificial Sequence
<220> FEATURE:
<223> OTHER INFORMATION: sdAb 34-1

<400> SEQUENCE: 17

```
caggtaaagc tggaggagtc tgggggaggc ttggtgcagc ctgggggtc tctgaggctc      60
tcctgtgcag cctctggaag catcttcagt atcaatgaca tgggctggta ccgccaggct    120
ccggggaagc agcgcgagtt ggtcgcacgt attactcgtg acggtagtgc tgcctatgaa    180
gactccgtga agggccgatt caccatctcc agagacaacg ccccgaacac ggtatttctg    240
caaatgaacg gcctgaaacc tgaggacacg gccgtctatt actgtaatgc agagattatt    300
actactcaga ctctgggtcg catgctgggg gagtattggg gacaggggac ccaggtcacc    360
gtctcctcag ccaggccgg ccagggatcc gaacaaaaac tgatcagcga agaagatctg    420
aaccatcacc atcaccatca c                                            441
```

<210> SEQ ID NO 18
<211> LENGTH: 147
<212> TYPE: PRT
<213> ORGANISM: Artificial Sequence
<220> FEATURE:
<223> OTHER INFORMATION: sdAb 34-1

<400> SEQUENCE: 18

```
Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Tyr Arg Gln Ala Pro Gly Lys Gln Arg Glu Leu Val
        35                  40                  45

Ala Arg Ile Thr Arg Asp Gly Ser Ala Ala Tyr Glu Asp Ser Val Lys
    50                  55                  60

Gly Arg Phe Thr Ile Ser Arg Asp Asn Ala Pro Asn Thr Val Phe Leu
65                  70                  75                  80

Gln Met Asn Gly Leu Lys Pro Glu Asp Thr Ala Val Tyr Tyr Cys Asn
                85                  90                  95

Ala Glu Ile Ile Thr Thr Gln Thr Leu Gly Arg Met Leu Gly Glu Tyr
            100                 105                 110

Trp Gly Gln Gly Thr Gln Val Thr Val Ser Ser Gly Gln Ala Gly Gln
        115                 120                 125

Gly Ser Glu Gln Lys Leu Ile Ser Glu Glu Asp Leu Asn His His His
    130                 135                 140

His His His
145
```

<210> SEQ ID NO 19
<211> LENGTH: 10
<212> TYPE: PRT
<213> ORGANISM: Artificial Sequence
<220> FEATURE:
<223> OTHER INFORMATION: c-Myc tag

<400> SEQUENCE: 19

```
Glu Gln Lys Leu Ile Ser Glu Glu Asp Leu
1               5                   10
```

```
<210> SEQ ID NO 20
<211> LENGTH: 6
<212> TYPE: PRT
<213> ORGANISM: Artificial Sequence
<220> FEATURE:
<223> OTHER INFORMATION: His tag

<400> SEQUENCE: 20

His His His His His His
1               5

<210> SEQ ID NO 21
<211> LENGTH: 11
<212> TYPE: PRT
<213> ORGANISM: Artificial Sequence
<220> FEATURE:
<223> OTHER INFORMATION: linker

<400> SEQUENCE: 21

Gly Pro Gly Gly Gly Ser Gly Gly Gly Gly Ser
1               5                   10

<210> SEQ ID NO 22
<211> LENGTH: 34
<212> TYPE: DNA
<213> ORGANISM: Artificial Sequence
<220> FEATURE:
<223> OTHER INFORMATION: primer MJ7

<400> SEQUENCE: 22
catgtgtaga ctcgcggccc agccggccat ggcc                              34

<210> SEQ ID NO 23
<211> LENGTH: 47
<212> TYPE: DNA
<213> ORGANISM: Artificial Sequence
<220> FEATURE:
<223> OTHER INFORMATION: primer MJ8

<400> SEQUENCE: 23
catgtgtaga ttcctggccg gcctggcctg aggagacggt gacctgg                47

<210> SEQ ID NO 24
<211> LENGTH: 38
<212> TYPE: DNA
<213> ORGANISM: Artificial Sequence
<220> FEATURE:
<223> OTHER INFORMATION: primer VHH BbsI

<400> SEQUENCE: 24
tatgaagaca ccaggcccag gtgcagctgg tggagtct                          38

<210> SEQ ID NO 25
<211> LENGTH: 31
<212> TYPE: DNA
<213> ORGANISM: Artificial Sequence
<220> FEATURE:
<223> OTHER INFORMATION: primer VHH-BamHI

<400> SEQUENCE: 25
cgcgggatcc tgaggagacg gtgacctggg t                                 31
```

ANTI-ICAM-1 SINGLE DOMAIN ANTIBODY AND USES THEREOF

This application is a national entry of International Patent Application PCT/CA2011/000481 filed Apr. 27, 2011 and claims the benefit of U. S. Provisional Patent Application USSN 61/328,406 filed Apr. 27, 2010, the entire contents of both of which are hereby incorporated by reference.

FIELD OF THE INVENTION

The present invention relates to anti-ICAM-1 single-domain antibodies and uses thereof. More specifically, the invention relates to anti-ICAM-1 single-domain antibodies and their use as diagnostic tools.

BACKGROUND OF THE INVENTION

Cardiovascular diseases are currently the leading cause of death in developed countries, and represent a growing financial burden on health care. Atherosclerosis, the narrowing of major arteries by fatty plaques, constitutes the single most important contributor to this group of diseases. However, in over half of affected individuals, the condition is left undetected and the earliest clinical manifestations are myocardial infarction, stroke, or sudden death. In particular, carotid artery stenosis (carotid artery disease—CAD), is responsible for approximately half of ischemic strokes, and is mostly caused by carotid atherosclerosis.

Landmark clinical trials over the past two decades have demonstrated that surgical intervention in cases of symptomatic high-grade stenosis can reduce the risk of subsequent stroke (Barnett et al, 1998; Ferguson et al 1999; Gillard, 2003). However, it has also been shown that the degree of stenosis is not predictive of risk for stroke; it is rather the presence of unstable, inflamed atherosclerotic plaques that is a more accurate predictor of impending stroke. Therefore, screening patients diagnosed with CAD for carotid atherosclerosis is recommended; however, such screening (MRI or X-ray angiography) might be costly.

Surgical treatment for CAD is performed via a procedure called endarterectomy, which typically comprises surgical removal of plaques from the artery, but unfortunately carries a high mortality risk of 2-10%. To justify such a high mortality risk and qualify patients for high-risk endarcterectomy, it is necessary to more accurately diagnose CAD caused by unstable atherosclerotic plaques, which are predictive of stroke.

Most patients with ischemic stroke or transient ischemic attack are screened for internal carotid artery stenosis. The current standard of care for detecting carotid stenosis is based on conventional imaging techniques such as ultrasound and angiography. These methods provide information about the structural consequences of CAD, such as luminal stenosis, but yield little to no information about plaque development and plaque characteristics within the vessel wall. None of these imaging techniques is able to provide information on the molecular or cellular events within the plaque that predispose it to rupture (i.e., an unstable plaque), and hence predict the real risk for stroke.

X-ray angiography remains the current gold standard imaging technique; however, it has many limitations. Angiography simply images the lumen of the vessel, and fails to detect atherosclerotic lesions that do not protrude into the lumen and provides little information on atherosclerotic plaque composition. Thus, it cannot differentiate between unstable and stable plaques and, therefore, is unable to predict the risk of plaque rupture. Consequently, because it is mostly symptom-driven, its main value is in delineating the causative lesion in a symptomatic patient. However, because of positive remodelling, a 'normal' angiogram cannot be interpreted as indicating an absence of atherosclerosis. Moreover, MRI and x-ray angiography screenings are costly.

Therefore, there remains a need in the art for a cost-effective method of screening atherosclerotic plaques to identify unstable plaques and more accurately predict the risk of rupture for heart attack and stroke.

SUMMARY OF THE INVENTION

The present invention relates to anti-ICAM-1 single-domain antibodies and uses thereof. More specifically, the invention relates to anti-ICAM-1 single-domain antibodies and their use as diagnostic tools.

The present invention provides an isolated or purified antibody or fragment thereof specific to intercellular adhesion molecule 1 (ICAM-1), comprising the sequence of complementarity determining region (CDR1) selected from sequences LYVMG (SEQ ID NO:1), AFRMG (SEQ ID NO:2), and INDMG (SEQ ID NO:3);

the sequence of CDR2 selected from sequences DITSSG-SIYYVDSLKG (SEQ ID NO:4), VITAGGTTSYIDS-VKG (SEQ ID NO:5), and RITRDGSAAYEDSVKG (SEQ ID NO:6); and the sequence of CDR3 selected from sequences HVRQDSGSEYLTY (SEQ ID NO:7), IDYDS (SEQ ID NO:8), and EIITTQTLGRMLGEY (SEQ ID NO:9).

The antibody or fragment thereof may have a CDR1 of sequence LYVMG (SEQ ID NO:1), a CDR2 of sequence DITSSGSIYYVDSLKG (SEQ ID NO:4), and a CDR3 of sequence HVRQDSGSEYLTY (SEQ ID NO:7). Alternatively, the antibody or fragment thereof may have a CDR1 of sequence AFRMG (SEQ ID NO:2), a CDR2 of sequence VITAGGTTSYIDSVKG (SEQ ID NO:5), and a CDR3 of sequence IDYDS (SEQ ID NO:8). In yet another alternative, the antibody or fragment thereof may have a CDR1 of sequence INDMG (SEQ ID NO:3), a CDR2 of sequence RITRDGSAAYEDSVKG (SEQ ID NO:6), and a CDR3 of sequence EIITTQTLGRMLGEY (SEQ ID NO:9).

The isolated or purified antibody or fragment thereof may be a single-domain antibody (sdAb); the sdAb may be of camelid origin. In one specific, non-limiting example, the isolated or purified antibody or fragment thereof may comprise the sequence:

```
                                          (SEQ ID NO: 10)
QVQLVESGGGLVQPGGSLRLSCAASGSISSLYVMGWYRQAPGKQRELV

ADITSSGSIYYVDSLKGRFTISRDNARSTVYLQMNSLEPEDTAVYYCM

AHVRQDSGSEYLTYWGQGTQVTVSS,
                                          (SEQ ID NO: 11)
QVKLEESGGGLVQAGDSLRLSCAASGRTVNAFRMGWYRQAPGKQRERV

AVITAGGTTSYIDSVKGRFTISRDNAKNTVYLQMNSLKPEDTAVYYCA

AIDYDSRGQGTQVTVSS,
or
                                          (SEQ ID NO: 12)
QVKLEESGGGLVQPGGSLRLSCAASGSIFSINDMGWYRQAPGKQRELV

ARITRDGSAAYEDSVKGRFTISRDNAPNTVFLQMNGLKPEDTAVYYCN

AEIITTQTLGRMLGEYWGQGTQVTVSS,
``` or a sequence substantially identical thereto.

The invention also provides nucleic acid sequences encoding the anti-ICAM-1 antibody or fragment thereof of the present invention, and vectors comprising the nucleic acid sequences.

The present invention further provides a targeted therapeutic agent comprising an antibody or fragment thereof of the present invention linked to a suitable therapeutic. The antibody or fragment thereof may serve to target therapeutic agents to the site of atherosclerotic plaques, or may have use as a therapeutic agent itself. In a non-limiting example, the antibody or fragment thereof or targeted therapeutic agent may be used for: therapeutically modifying the inflammatory component of atherosclerotic disease (e.g., stroke prevention therapy), or to treat conditions associated with increased ICAM-1 expression.

The present invention further provides a molecular imaging agent comprising an antibody or fragment thereof in accordance with the present invention linked to a detectable agent. For example, the anti-ICAM-1 or fragment thereof may be linked to a radioisotope, a paramagnetic label, a fluorophore, an echogenic microbubble, an affinity label (for example biotin, avidin, etc), or any other suitable agent that may be detected by diagnostic imaging methods. In a specific, non-limiting example, the anti-ICAM-1 or fragment thereof may be linked to a near infrared fluorescence (NIRF) imaging dye, for example and not wishing to be limiting Cy5.5, Alexa680, Dylight680, or Dylight800 or ICG.

The present invention also provides an ex vivo method of detecting atherosclerotic plaque diseases involving inflammation, comprising:
a) providing a tissue sample suspected of inflammation and plaque formation;
b) contacting said sample with an anti-ICAM-1 antibody or fragment thereof of the present invention under suitable conditions; and
c) detecting the formation of a protein complex,
wherein the anti-ICAM-1 antibody or fragment thereof binds to the tissue sample comprising atherosclerotic plaque formation at a higher rate than that of a control sample. The tissue sample may be any suitable tissue sample, for example but not limited to a vascular tissue sample or a brain tissue sample. The step of detecting (step c) may be accomplished by a any suitable molecular diagnostic imaging method including, but not limited to optical imaging, molecular diagnostic imaging or immunohistochemistry, or ELISA.

The present invention also provides an in vivo method of detecting atherosclerotic plaque diseases involving inflammation, comprising:
a) administering the molecular imaging agent of the present invention to a subject; and
b) detecting the binding of the molecular imaging agent,
wherein the molecular imaging agent binds to binds ICAM-1 in vivo at a detectably higher rate than the rate of binding to normal vasculature, and wherein the binding of molecular imaging agent to the vasculature is indicative of the presence of atherosclerotic plaques. The step of detecting (step b) may be accomplished by a non-invasive (molecular) diagnostic imaging method including, but not limited to optical imaging, ultrasound, MRI, PET, and SPECT.

The present invention also provides a method of detecting conditions characterized with increased expression of ICAM-1, comprising:
a) administering a molecular imaging agent of the present invention to a subject of interest;
b) detecting the molecular imaging agent in vivo,
wherein the molecular imaging agent binds to binds ICAM-1 in vivo at a detectably higher rate than the rate of binding to normal tissue. The method may be a non-invasive (molecular) diagnostic imaging method including, but not limited to optical imaging, ultrasound, MRI, PET, and SPECT. Conditions associated with increased ICAM-1 expression may include, but are not limited to carotid artery disease, stroke, myocardial infarction, inflammatory bowel disease, autoimmune diseases, multiple sclerosis, Crohn's disease, and neovascularization associated with tumour angiogenesis.

The in vivo detection step in the methods described above may be whole body imaging for diagnostic purposes or local imaging at specific sites, such as carotid and aortic arteries, in a quantitative manner to assess the progression of disease or host response to a treatment regimen.

The methods as described herein may be used to monitor the progression or regression of disease over time. The methods described herein may also be used to monitor the efficacy of therapy, for example but not limited to drugs such as statins in the treatment of atheroslerosis.

The present invention further provides a method for diagnosing a clinical condition associated with ICAM-1 overexpression in a patient, said method comprising administering an effective amount of the molecular imaging agent of the present invention to the patient and detecting any ICAM-1 bound to the imaging agent. The clinical condition may be vascular inflammation, stroke, cancer, or angiogenesis. The step of detecting may be accomplished by non-invasive optical imaging, ultrasound, MRI, PET, or SPECT.

Anti-ICAM-1 single-domain antibodies were obtained by immunization of a llama with ICAM-1; three clones in particular were shown to specifically bind ICAM-1. The anti-ICAM-1 sdAb were coupled with the near infrared fluorescence (NIRF) imaging dye for application, which was advantageous in optical imaging due to the conjugate's high sensitivity and avoidance of ionizing radiation. Using this formulation, it was shown that the NIRF-labelled anti-ICAM-1 sdAb specifically recognized early and developed atherosclerotic plaques in large vessels in high-fat diet fed ApoE KO mice; it was additionally shown that this can be monitored non-invasively by prospective optical imaging in vivo. The distribution of the ICAM-1 sdAb in the plaques was confirmed using microscopic techniques and immunohistochemistry.

The use of sdAb is advantageous as they may be produced easily and inexpensively in large quantities, as opposed to antibodies produced from hybridoma cell lines. Additionally, hybridoma lines may be unstable and decrease antibody expression levels over time. sdAb are also advantageous for molecular imaging applications due to their short plasma half-life, which achieves fast contrast-to-noise ratio needed for imaging.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 2 shows the nucleotide (SEQ ID NO:13) and amino acid (SEQ ID NO:14) sequences of anti-ICAM sdAb clone 11-4, including c-Myc (underlined) and histidine tags (bolded).

FIG. 3 shows the nucleotide (SEQ ID NO:15) and amino acid (SEQ ID NO:16) sequences of anti-ICAM sdAb clone 5-5, including c-Myc (underlined) and histidine tags (bolded).

FIG. 4 shows the nucleotide (SEQ ID NO:17) and amino acid (SEQ ID NO:18) sequences of anti-ICAM sdAb clone 34-1, including c-Myc (underlined) and histidine tags (bolded).

FIG. 16 shows results of a three-dimensional analysis of the optical signal in ApoE KO mice 6 months after start of a high-fat diet. The mice were injected with 50 μg anti-ICAM-1 sdAb 11-4 labelled with Cy5.5 48 h prior to imaging. The 3D reconstruction (FIG. 16B) confirms that high fluorescence intensity (optical; FIG. 16A) signal originates from the heart and thoracic aorta region characterized with high atherosclerotic deposits.

Cy5.5 (right panel) co-localizes with atherosclerotic plaques in frozen sections of aorta in ApoE KO mice. No anti-ICAM-1 sdAb 11-4-Cy5.5 signal was observed in aortas of control mice (Arrows point to the localization of ICAM-1).

Figure 26:
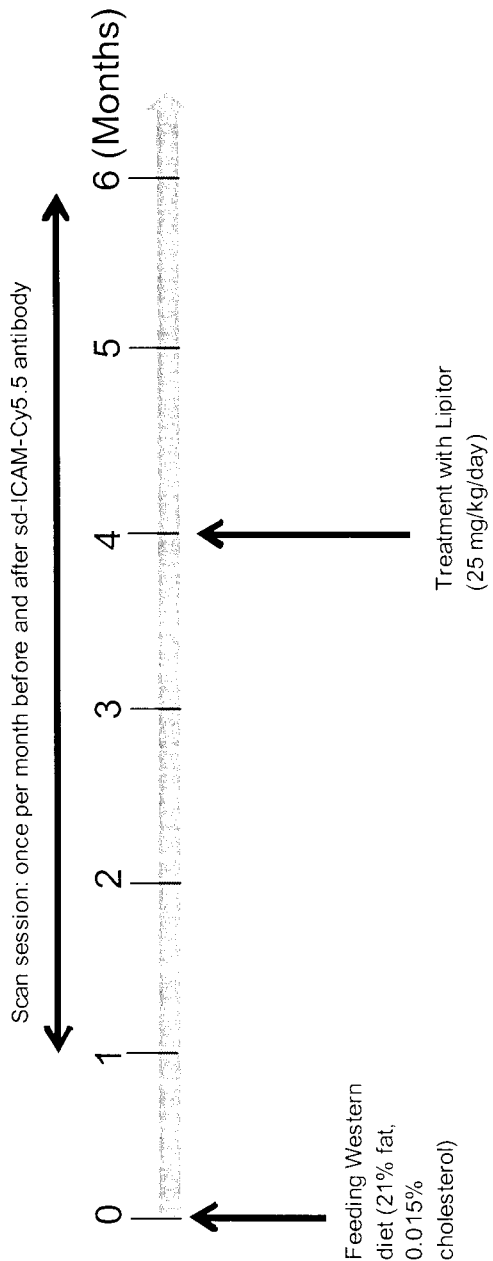

FIG. 26 is a schematic describing the in vivo optical imaging protocol for scanning ApoE KO mice and control mice. It shows the times of scanning and starting of Atorvastatin (Lipitor) treatment to reduce atherosclerosis.

Figure 27:
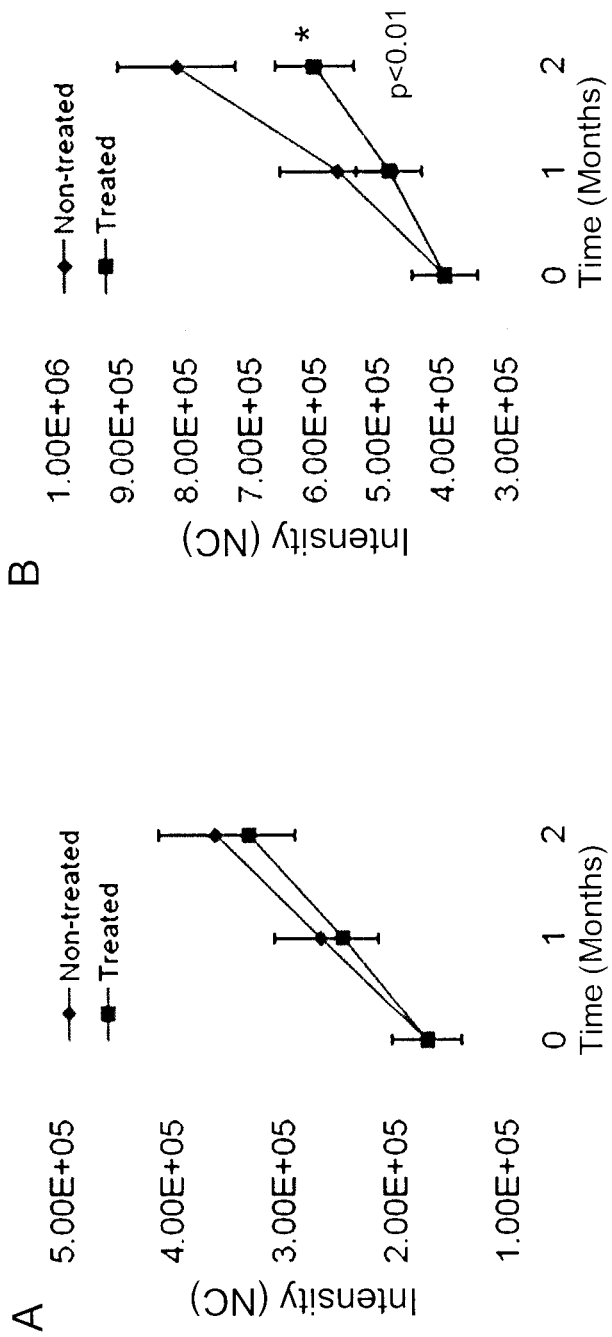

FIG. 27 are graphs representing data obtained while monitoring of atherosclerotic disease response to Atorvastatin (Lipitor) using anti-ICAM-1 sdAb 11-4. Quantification of fluorescence intensity signal is shown in non-treated and Atorvastatin-treated control (FIG. 29A) and ApoE KO animals (FIG. 29B). Atorvastatin (Lipitor) was administered at 25 mg/kg/day for 2 months. The mice were injected with 50 µg anti-ICAM-1 sdAb 11-4 labelled with Cy5.5 48 h prior to imaging at indicated time points after the start of high-fat diet. Fluorescence was quantified in heart/aorta ROI. Atorvastatin-treated ApoE KO animals demonstrate reduction of fluorescence signal compared to non-treated ApoE KO animals.

Figure 28:
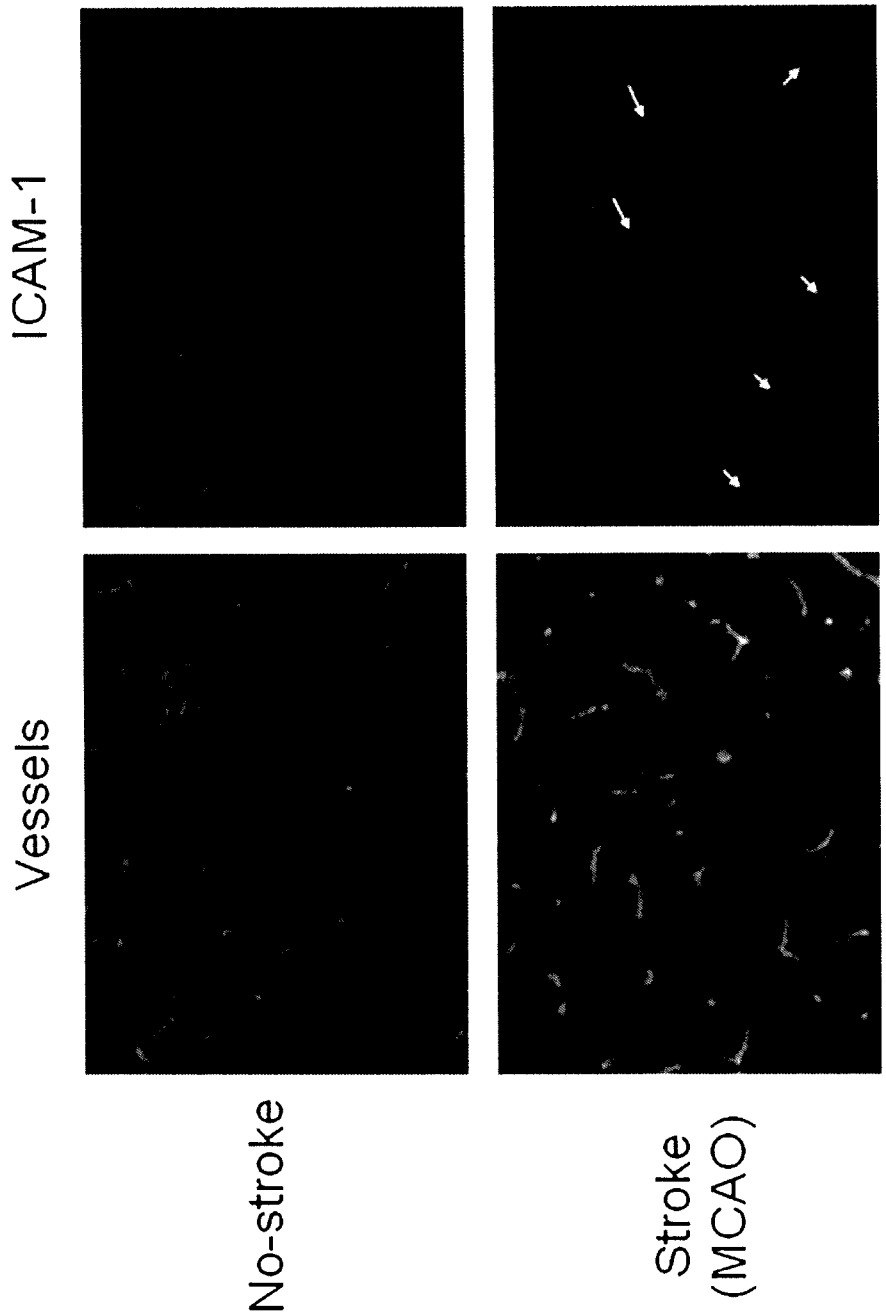

FIG. 28 shows immunofluorescence images of ICAM-1 expression (right panels) in brain vessels (left panels) in control animals (upper panels) and after experimental stroke (middle cerebral artery occlusion; MCAO) (bottom panels). Arrows show ICAM-1 expressing brain vessels after stroke.

Figure 29:
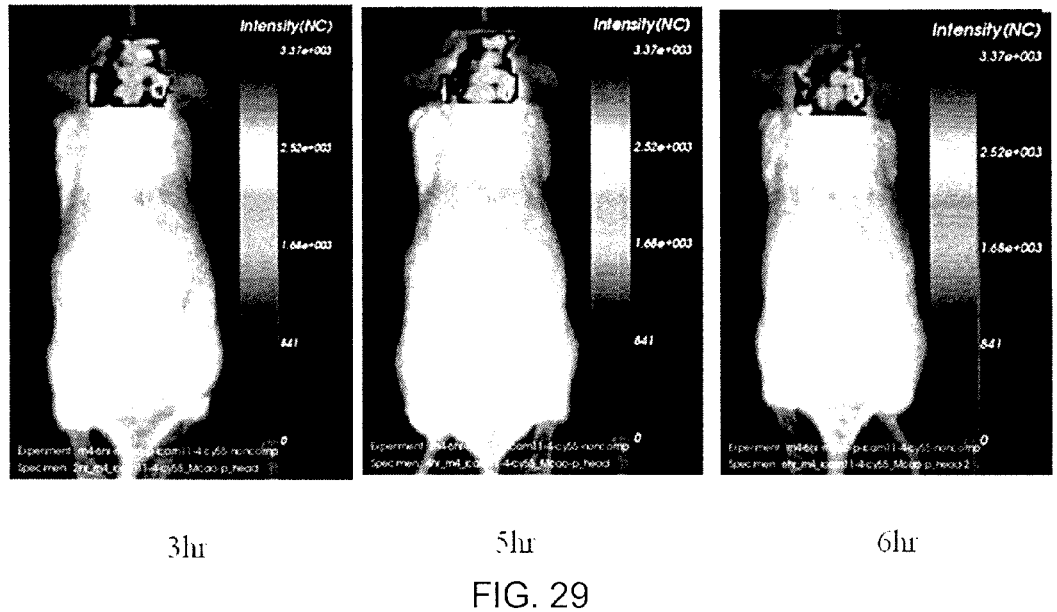

FIG. 29 shows in vivo head imaging after permanent left middle cerebral artery occlusion (MCAO) using anti-ICAM-1 11-4 sdAb-Cy5.5. The anti-ICAM-1 sdAb labeled with Cy5.5 near infrared fluorophore was injected in the tail vein (50 microgram) in mice that have undergone left permanent MCAO for 1 hour. Head region of mice was imaged up to 6 hour post-injection. Results show high fluorescence signal in the right side of the head, contralateral to the side of permanent MCAO.

Figure 30:
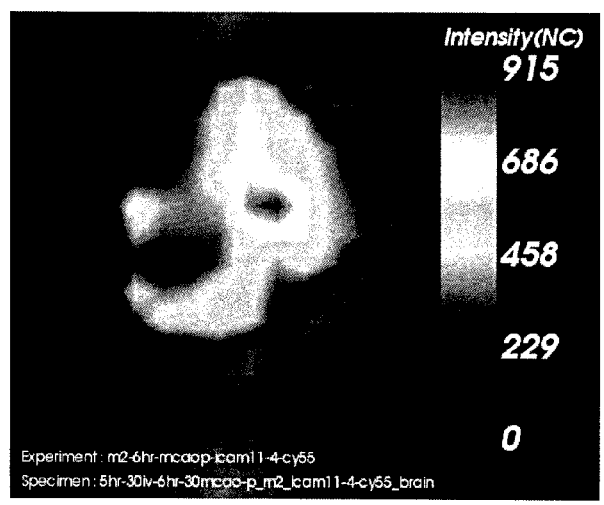

FIG. 30 shows ex vivo brain imaging after permanent MCAO using anti-ICAM-1 11-4 sdAb-Cy5.5. The anti-ICAM-1 sdAb labeled with Cy5.5 near infrared fluorophore was injected in the tail vein (50 microgram) in mice that have undergone left permanent MCAO for 1 hour. Ex vivo brain imaging was performed 6 h after injection and shows fluorescent signal in the right side of the brain contralateral to permanent MCAO (infarct region lacking fluorescent signal).

Figure 31:
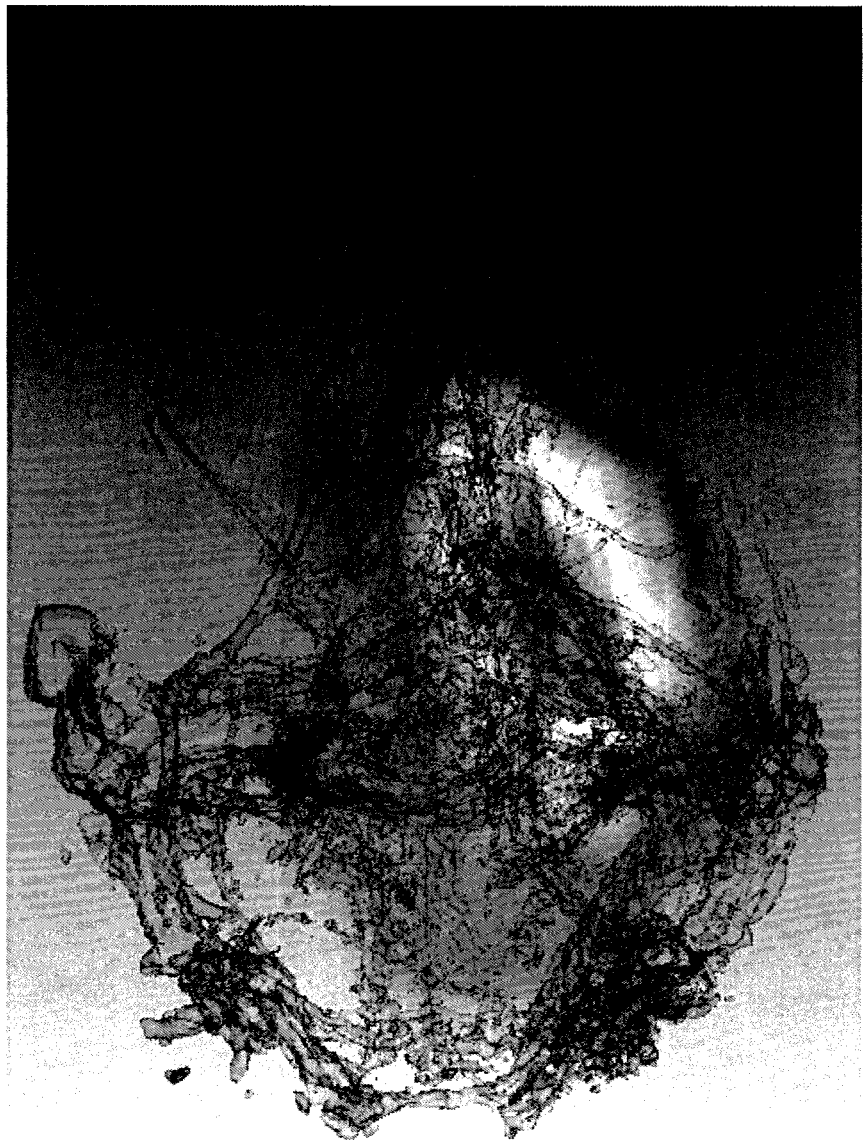

FIG. 31 shows multi-modal molecular imaging of vascular activation using anti-ICAM-1 11-4 sdAb in permanent MCAO. Animals with left permanent MCAO were injected with 50 µg of anti-ICAM-1 sdAb labeled with Cy5.5 near infrared fluorophore. Animals were optically imaged at 6 hour post-injection. Animals were then perfused with microfill to visualize the brain vascular bed using microcomputed tomography. The molecular optical image indicative of increased ICAM-1 expression detected using anti-ICAM-1 sdAb was co-registered with the brain vessel map generated by microcomputed tomography to obtain a better anatomical localization of the molecular signal.

DETAILED DESCRIPTION OF THE INVENTION

The present invention relates to anti-ICAM-1 single-domain antibodies and uses thereof. More specifically, the invention relates to anti-ICAM-1 single-domain antibodies and their use as diagnostic tools.

The present invention is directed to anti-intercellular adhesion molecule 1 (ICAM-1) antibodies and molecular imaging agents based on the antibodies. The present invention also covers methods and applications for non-invasive molecular imaging of atherosclerotic disease, which may provide information on plaque status (stable, active, inflamed, etc) based on molecular characteristics or processes within the plaque. The methods as described herein may be use to monitor the progression or regression of disease over time, or to monitor the efficacy of therapy.

The present invention provides an isolated or purified antibody or fragment thereof specific to intercellular adhesion molecule 1 (ICAM-1), comprising
    the sequence of complementarity determining region (CDR) 1 selected from sequences LYVMG (SEQ ID NO:1), AFRMG (SEQ ID NO:2), and INDMG (SEQ ID NO:3);
    the sequence of CDR2 selected from sequences DITSSG-SIYYVDSLKG (SEQ ID NO:4), VITAGGTTSYIDS-VKG (SEQ ID NO:5), and RITRDGSAAYEDSVKG (SEQ ID NO:6); and
    the sequence of CDR3 selected from sequences HVRQDSGSEYLTY (SEQ ID NO:7), IDYDS (SEQ ID NO:8), and EIITTQTLGRMLGEY (SEQ ID NO:9).

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains; the numbering for the hypervariable loops is defined as H1: 27-35; H2: 52-56; and H3: 95-102 (equivalent to CDR3 of Kabat numbering) for VHNHH domains (Chothia and Lesk, 1987). As these individual schemes define CDR and hypervariable loop regions that are adjacent or overlapping, those of skill in the antibody art often utilize the terms "CDR" and "hypervariable loop" interchangeably, and they may be so used herein. The CDR amino acids in VH and VL regions are defined herein according to the Kabat numbering system (Kabat et al. 1991).

The region outside of the CDR is referred to as the framework region (FR). The FR provides structural integrity to the variable domain and ensure retention of the immunoglobulin fold. This characteristic structure of antibodies provides a stable scaffold upon which substantial antigen-binding diversity can be explored by the immune system to obtain specificity for a broad array of antigens (Padlan et al, 1994).

An "antibody fragment" as referred to herein may include any suitable antigen-binding antibody fragment known in the art. The antibody fragment may be obtained by manipulation of a naturally-occurring antibody, or may be obtained using recombinant methods. For example, an antibody fragment may include, but is not limited to Fv, single-chain Fv (scFV; a molecule consisting $V_L$ and $V_H$ connected with a peptide linker), Fab, Fab', F(ab')$_2$, single domain antibody (sdAb), and multivalent presentations of these.

In a non-limiting example, the antibody fragment may be a single domain antibody (sdAb) derived from naturally-occurring sources. Heavy chain antibodies of camelid origin (Hamers-Casterman et al, 1993) lack light chains and thus their antigen binding sites consist of one domain, termed $V_HH$. sdAb have also been observed in shark and are termed VNARs (Nuttall et al, 2003); other sdAb may be engineered based on human heavy or light chain sequences (Jespers et al, 2004; To et al, 2005). As used herein, "sdAb" includes those directly isolated from $V_L$, $V_H$, $V_HH$ or $V_{NAR}$ reservoir of any origin through phage display or other display technologies and those generated through further modification of such sdAb by humanization, affinity maturation, stabilization, solubilisation (e.g., camelization), or other methods of antibody engineering. Also encompassed by the present invention are homologues, derivatives, or fragments that retain the antigen-binding function and specificity of the sdAb.

A person of skill in the art would be well-acquainted with the structure of a single-domain antibody (see, for example, 3DWT, 2P42 in Protein Data Bank). A sdAb comprises a single immunoglobulin domain that retains the immuglobulin fold; most notably, only three CDR form the antigen-binding site. However, not all CDR may be required for binding the antigen. For example, and without wishing to be limiting, one, two, or three of the CDR may contribute to binding and recognition of the antigen by the sdAb of the present invention. The CDR of the sdAb are referred to herein as CDR1, CDR2, and CDR3, and are based on Kabat numbering (Kabat et al. 1991).

The terms "antibody" and "antibody fragment" ("fragment thereof") are as defined above. As previously stated, the antibody or fragment thereof may be a sdAb. The sdAb may be of camelid origin, and thus may be based on camelid framework regions; alternatively, the CDR may be grafted onto the framework regions of other antibody domains, for example but not limited to VNAR, human $V_H$ or human $V_L$ framework regions. In yet another alternative, the CDR described above may be grafted onto the framework regions of other types of antibody fragments (Fv, scFv, Fab). The present embodiment further encompasses an antibody fragment that is "humanized" using any suitable method know in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., ICAM-1) is also preserved. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would be amply familiar with methods of preparing such humanized antibody fragments.

By "specific to ICAM-1", it is meant that the antibody or fragment thereof of the present invention recognizes and binds to intercellular adhesion molecule 1 (ICAM-1), also referred to in the art as CD54. ICAM-1 is a cell adhesion molecule in the immunoglobulin superfamily expressed on the surface of endothelial cells. ICAM-1 is normally expressed in low levels in endothelial cells. However, in inflammatory conditions (e.g., the presence of inflammatory cytokines such as TNF-α, interferon-γ, interleukin-4 and interleukin-1β), the level of expression is rapidly increased on the surface of endothelial cells; ICAM-1 plays a role in inflammatory cell (leukocytes) adhesion to endothelial cells and their recruitment into inflamed tissues. ICAM-1 also mediates the firm adhesion of lymphocytes, monocytes and neutrophils to the sites of endothelial lesion development. Therefore, the expression of ICAM-1 plays an important rote in the amplification of inflammation. ICAM-1 may be an early sign of endothelial activation and damage present before the onset of plaque formation (liyama et al, 1999).

The antibody or fragment thereof may have a CDR1 of sequence LYVMG (SEQ ID NO:1), AFRMG (SEQ ID NO:2), and INDMG (SEQ ID NO:3); a CDR2 of sequence DITSSGSIYYVDSLKG (SEQ ID NO:4), VITAGGTTSYIDSVKG (SEQ ID NO:5), and RITRDGSAAYEDSVKG (SEQ ID NO:6); and a CDR3 of sequence HVRQDSGSEYLTY (SEQ ID NO:7), IDYDS (SEQ ID NO:8), and EIITTQTLGRMLGEY (SEQ ID NO:9). The antibody or fragment thereof may be a sdAb. The sdAb may be of camelid origin, and thus may be based on camelid framework regions; alternatively, the CDR may be grafted onto other antibody domains, for example but not limited to VNAR or human $V_HH$ framework regions.

In a non-limiting example, the antibody or fragment thereof may have a CDR1 of sequence LYVMG (SEQ ID NO:1), a CDR2 of sequence DITSSGSIYYVDSLKG (SEQ ID NO:4), and a CDR3 of sequence HVRQDSGSEYLTY (SEQ ID NO:7). Alternatively, the antibody or fragment thereof may have a CDR1 of sequence AFRMG (SEQ ID NO:2), a CDR2 of sequence VITAGGTTSYIDSVKG (SEQ ID NO:5), and a CDR3 of sequence IDYDS (SEQ ID NO:8). In yet another alternative, the antibody or fragment thereof may have a CDR1 of sequence INDMG (SEQ ID NO:3), a CDR2 of sequence RITRDGSAAYEDSVKG (SEQ ID NO:6), and a CDR3 of sequence EIITTQTLGRMLGEY (SEQ ID NO:9).

In one specific, non-limiting example, the isolated or purified antibody or fragment thereof may comprise the sequence:

(SEQ ID NO: 10)
QVQLVESGGGLVQPGGSLRLSCAASGSISSLYVMGWYRQAPGKQRELV

ADITSSGSIYYVDSLKGRFTISRDNARSTVYLQMNSLEPEDTAVYYCM

AHVRQDSGSEYLTYWGQGTQVTVSS, (SEQ ID NO: 11)
QVKLEESGGGLVQAGDSLRLSCAASGRTVNAFRMGWYRQAPGKQRERV

AVITAGGTTSYIDSVKGRFTISRDNAKNTVYLQMNSLKPEDTAVYYCA

AIDYDSRGQGTQVTVSS,
or (SEQ ID NO: 12)
QVKLEESGGGLVQPGGSLRLSCAASGSIFSINDMGWYRQAPGKQRELV

ARITRDGSAAYEDSVKGRFTISRDNAPNTVFLQMNGLKPEDTAVYYCN

AEIITTQTLGRMLGEYWGQGTQVTVSS, or a sequence substantially identical thereto. In a specific, non-limiting example, the isolated or purified antibody or fragment thereof may also comprise the sequence of clone 11-4, 5-5, or 34-1 as shown in FIGS. 2 to 4, or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides.

Conservative amino acid mutation may include addition, deletion, or substitution of an amino acid; in one non-limiting example, the conservative amino acid mutation is a conservative amino acid substitution. A conservative amino acid substitution is defined herein as the substitution of an amino acid residue for another amino acid residue with similar chemical properties (e.g. size, charge, or polarity).

A conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "nonpolar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G).

"Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 70% identical; in another example, the substantially identical sequences may be at least 70, 71, 72, 73, 74, 75, 80, 85, 90, 91, 92, 93, 94, 95, 96, 97, 98, 99, or 100% identical at the amino acid level to sequences described herein. Importantly, the substantially identical sequences retain the activity and specificity of the reference sequence. For example, and without wishing to be limiting, the degree of identity between clones 11-4 and 5-5, clones 5-5 and 34-1 is 70%; the degree of identity between clones 11-4 and 34-1 is 75%. As would be know to one of skill in the art, amino acid residues of an antibody, particularly within the framework regions may be mutated (substituted or deleted) without affecting the functional properties of the antibody (antigen recognition and binding).

The antibody or fragment thereof of the present invention may also comprise additional sequences to aid in expression, detection, or purification of a recombinant antibody or fragment thereof. For example, and without wishing to be limiting, the antibody or fragment thereof may comprise a targeting or signal sequence (for example, but not limited to ompA), a detection tag (for example, but not limited to c-Myc, EQKLISEEDL, SEQ ID NO:19), a purification tag (for example, but not limited to a histidine purification tag, HHHHHH, SEQ ID NO:20), or any combination thereof.

The antibody or fragment thereof of the present invention may also be in a multivalent display. Multimerization may be achieved by any suitable method of know in the art. For example, and without wishing to be limiting in any manner, multimerization may be achieved using self-assembly molecules (Zhang et al, 2004; Merritt & Hol, 1995), as described in WO2003/046560. The described method produces pentabodies by expressing a fusion protein comprising the antibody or fragment thereof of the present invention and the pentamerization domain of the B-subunit of an $AB_5$ toxin family (Nielson et al, 2000); the pentamerization domain assembles into a pentamer, through which a multivalent display of the antibody or fragment thereof is formed. Each subunit of the pentamer may be the same or different. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody. In one non-limiting example, the linker may be the linker GPGGGSGGGGS (SEQ ID NO:21)

Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielsen et al, 1996), c-jun/Fos interaction (de Kruif et al, 1996), "Knob into holes" interaction (Ridgway et al, 1996).

Another method known in the art for multimerization is to dimerize the antibody or fragment thereof using a Fc domain. In this approach, a Fc gene in inserted into an expression vector; the nucleotide sequence of the antibody or fragment thereof can be amplified and inserted into the vector such that the C-terminus of the antibody or fragment thereof is linked to the hinge region of the Fc without addition of extra residues. The resulting vector can be transfected to cells and the fusion protein may be recombinantly expressed, then purified by affinity chromatography (for example, on a protein A column). One non-limiting example of such a method of multimerization is described by Bell et al (2010) and Iqbal et al (in press). Techniques for implementing such dimerization would be known to those of skill in the art.

The present invention also encompasses nucleic acid sequences encoding the molecules as described herein. The nucleic acid sequence may be codon-optimized. The present invention also encompasses vectors comprising the nucleic acids as just described.

The present invention further provides a targeted therapeutic agent comprising an anti-ICAM-1 antibody or fragment thereof of the present invention linked to a suitable therapeutic. The antibody or fragment thereof may serve to target therapeutic agents to the site of atherosclerotic plaques, or may have use as a therapeutic agent itself. For example, and without wishing to be limiting, the antibody or fragment thereof may be used for therapeutically modifying the inflammatory component of atherosclerotic disease (e.g., stroke prevention therapy). Additionally, the antibody or fragment thereof or the targeted therapeutic agent may be used to treat conditions associated with increased ICAM-1 expression; these may include, but are not limited to carotid artery disease, stroke, myocardial infarction, inflammatory bowel disease, autoimmune diseases, multiple sclerosis, Crohn's disease, and neovascularization associated with tumour angiogenesis. For example, and without wishing to be limiting in any manner, the therapeutic agent may be an anti-inflammatory drug, a cholesterol-lowering drug, or a plaque-stabilizing drug.

The present invention also encompasses a molecular imaging agent comprising an anti-ICAM-1 antibody or fragment thereof in accordance with the present invention linked to a detectable agent. For example, the anti-ICAM-1 or fragment thereof may be linked to a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods. In a specific, non-limiting example, the anti-ICAM-1 or fragment thereof may be linked to a near infrared fluorescence (NIRF) imaging dye, for example and not wishing to be limiting Cy5.5, Alexa680, Dylight680, or Dylight800.

An ideal molecular imaging agent for imaging atherosclerotic plaque diseases, such as carotid atherosclerosis, should have a high sensitivity and specificity for the detection of plaques, and provide information about the probability of adverse outcome in both symptomatic and asymptomatic individuals. Because baseline constitutive ICAM-1 expression is low, it is expressed on the luminal surface of endothelial cells, and the expression levels correlate with the severity of disease (Kitagawa et al, 2002), ICAM-1 is an excellent target for non-invasive molecular imaging applications to diagnose pre-symptomatic and/or unstable carotid artery disease and other atherosclerotic plaque diseases. To obtain clear images, it is imperative that molecular imaging agent has rapid clearance from the circulation and high target (atherosclerotic plaque)-to-background (blood pool) ratio. Because of the fast clearance of antibody fragments, and single domain antibodies in particular, and their short half life, they are superior to whole IgG molecules in achieving a successful image. Additionally, the coupling of single domain antibodies against ICAM-1 to a Near Infrared Fluorescence (NIRF) imaging dye for optical imaging is advantageous due to high sensitivity and avoidance of ionizing radiation.

The therapeutic agent or detectable agent may be linked to the anti-ICAM-1 antibody or fragment thereof by any method know in the art. By the term "linked", also referred to herein as "conjugated", it is meant that the antibody or fragment thereof is linked directly or indirectly (e.g., via a linker), covalently or non-covalently (e.g., adsorption, ionic interaction) to the therapeutic or detectable agent. A covalent linkage may be achieved through a chemical cross-linking reaction, or through fusion using recombinant DNA methodology combined with any peptide expression system, such as bacteria, yeast or mammalian cell-based systems. Methods for linking an antibody or fragment thereof to a therapeutic agent or detectable agent would be well-known to a person of skill in the art.

The antibodies or fragments thereof and/or molecular imaging agents may be used in methods and applications for imaging of atherosclerotic disease, which may provide information on plaque status (stable, active, inflamed, etc) based on molecular characteristics/processes taking place within the plaque. Such information obtained in the realm of clinical diagnosis and triage would also present an opportunity to gain insight into the complex chain of events underlying atherogenesis, plaque progression, and ultimately atherothrombosis with accompanying clinical symptoms.

The present invention provides an ex vivo method of detecting atherosclerotic plaque diseases involving inflammation, comprising:
a) providing a tissue sample suspected of inflammation and plaque formation;
b) contacting said sample with an anti-ICAM-1 antibody or fragment thereof of the present invention under suitable conditions; and
c) detecting the formation of a protein complex, wherein the anti-ICAM-1 antibody or fragment thereof binds to the tissue sample comprising atherosclerotic plaque formation at a higher rate than that of a control sample.

The tissue sample in the method as just described may be any suitable tissue sample, for example but not limited to a serum sample, a vascular tissue sample or a brain tissue sample. The step of contacting (step b)) is done under suitable conditions, known to those skilled in the art, for formation of a complex between the antibody or fragment thereof and ICAM-1 protein. The control sample may be a corresponding tissue sample that does not exhibit increased ICAM-1 expression.

The step of detecting (step c)) may be accomplished by any suitable method known in the art, for example, but not limited to optical imaging, immunohistochemistry or molecular diagnostic imaging, ELISA, or other suitable method.

The invention also provides a method for analyzing the ICAM-1 expression in atherosclerotic plaques in vivo by means of non-invasive imaging using optical imaging techniques. The in vivo method of detecting atherosclerotic plaque diseases involving inflammation may comprise:
a) administering the molecular imaging agent of the present invention to a subject; and
b) detecting the binding of the molecular imaging agent, wherein the molecular imaging agent binds to binds ICAM-1 in vivo at a detectably higher rate than the rate of binding to normal vasculature, and wherein the binding of molecular imaging agent to the vasculature is indicative of the presence of atherosclerotic plaques. The method as just described may also be used for imaging atherosclerotic plaques The ability to use non-invasive molecular imaging techniques to detect or image atherosclerotic plaques may lead to early diagnosis (asymptomatic) of atherosclerosis. Additionally, prospective monitoring via molecular imaging of plaques would give insight regarding atherosclerotic disease progression/stability.

The present invention further provides a method of detecting conditions characterized by increased expression of ICAM-1, comprising:
  a) administering a molecular imaging agent of the present invention to a subject of interest;
  b) detecting the molecular imaging agent in vivo.
wherein the molecular imaging agent binds to binds ICAM-1 in vivo at a detectably higher rate than the rate of binding to normal tissue. As previously described, the level of expression of ICAM-1 is increased on the surface of endothelial cells in inflammatory conditions (e.g., the presence of inflammatory cytokines such as TNF-α, interferon-γ, interleukin-4 and interleukin-1β). Conditions associated with increased ICAM-1 expression may include, but are not limited to carotid artery disease, stroke, myocardial infarction, inflammatory bowel disease, autoimmune diseases, multiple sclerosis, Crohn's disease, and neovascularization associated with tumour angiogenesis.

The in vivo detection step in the methods described above may be whole body imaging for diagnostic purposes or local imaging at specific sites, such as but not limited to carotid arteries, in a quantitative manner to assess the progression of disease or host response to a treatment regimen. The detection step in the methods as described above may be immunohistochemistry, or a non-invasive (molecular) diagnostic imaging technology including, but not limited to:
  Optical imaging;
  Positron emission tomography (PET), wherein the detectable agent is an isotopes such as $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized;
  Single photon emission computed tomography (SPECT), wherein the detectable agent is a radiotracer such as $^{99m}$Tc, $^{111}$In, $^{123}$I, $^{201}$Tl, $^{133}$Xe, depending on the specific application;
  Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques.
  Contrast-Enhanced Ultrasonography (CEUS) or ultrasound, wherein the detectable agent is at least one acoustically active and gas-filled microbubble. Ultrasound is a widespread technology for the screening and early detection of human diseases. It is less expensive than MRI or scintigraphy and safer than molecular imaging modalities such as radionuclide imaging because it does not involve radiation.

The optimal dose of injection and method of administration (intravenous (i.v.), intraperitoneal (i.p), subcutenous (s.c.), oral, or nasal) are generally determined experimentally.

The methods described herein may be used to diagnose atherosclerosis, including early diagnosis (i.e., sub-clinical atherosclerosis), distinguish stable from unstable plaques, monitor the progression or regression of disease over time, and/or monitor the efficacy of therapy, for example but not limited to drugs such as statins in the treatment of atherosclerosis. To do so, the methods described herein may be combined with other data, for example, but not limited to atherosclerosis staging, atherosclerosis prognosis, and vascular inflammation levels.

Anti-ICAM-1 single-domain antibodies were obtained by immunization of a llama with ICAM-1; three clones in particular were shown to specifically bind ICAM-1. The anti-ICAM-1 sdAb were coupled with the near infrared fluorescence (NIRF) imaging dye for application, which was advantageous in optical imaging due to the conjugate's high sensitivity and avoidance of ionizing radiation. Using this formulation, it was shown that the NIRF-labelled anti-ICAM-1 sdAb specifically recognized early and developed atherosclerotic plaques in large vessels in high-fat diet fed ApoE KO mice; it was additionally shown that this can be monitored non-invasively by prospective optical imaging in vivo. The distribution of the anti-ICAM-1 sdAb in the plaques was confirmed using microscopic techniques and immunohistochemistry. Optical imaging as a means of imaging atherosclerosis in vivo provides a high sensitivity, allowing for detection at an earlier stage of the disease, which may potentially lead to better therapeutic outcomes.

The use of sdAb is advantageous as they may be produced easily and inexpensively in large quantities, as opposed to antibodies produced from hybridoma cell lines. Additionally, hybridoma lines may be unstable and decrease antibody expression levels over time. sdAb are also advantageous for molecular imaging applications due to their short plasma half-life, which achieves fast contrast-to-noise ratio needed for imaging.

The present invention will be further illustrated in the following examples. However, it is to be understood that these examples are for illustrative purposes only and should not be used to limit the scope of the present invention in any manner.

EXAMPLE 1

Immunization and PCR Amplification

Single-domain antibodies (sdAb) were generated by immunization of a llama with ICAM-1. Lymphocytes were collected and DNA corresponding to sdAb was purified.

A llama was immunized with recombinant antigen. For each injection, 100 µg of recombinant human ICAM-1 (R&D systems, reconstituted with sterile water according to manufacturer's recommendation to prepare a stock solution of 1 mg/ml), in a total volume of 0.5 ml was mixed with an equal volume of incomplete Freund's adjuvant and 0.5 ml was injected, subcutaneously. Seven injections were performed at approximately two week intervals and blood was collected at each injection.

Total RNA was isolated from approximately 1×10$^7$ lymphocytes collected from day 70 of the immunization protocol with a QIAamp RNA blood mini kit (QIAGEN Sciences, Mississauga, ON) and according to the kit instructions. About 5 µg of total RNA was used as template for first strand cDNA synthesis with an oligo dT primer using a first-strand cDNA synthesis kit (Amersham Biosciences, USA). Based on the camelidae and llama immunoglobulin databases, three variable domain sense primers (MJ1-3) and two CH2 domain antisense primers (CH2 and CH2b3) were designed (Doyle et al. 2008). The first PCR was performed with the cDNA as template and the variable regions of both conventional (IgG1) and heavy chain antibodies (IgG2 and IgG3) were amplified with combinations of MJ1-3/CH2 and MJ1-3/CH2b3 primers in two separate PCR reactions. The PCR reaction mixtures contained the following components: 2 µl cDNA, 5 pmol of MJ1-3 primer mixture, 5 pmol of either CH2 or CH2b3 primer, 5 µl of 10× reaction buffer, 3 µl of 2.5 mM dNTP, 2.5 units of Taq DNA polymerase (Roche Applied Science, Indianapolis, Ind.) and water to a final volume of 50 µl. The PCR protocol comprised an initial step at 94° C. for 3 min followed by 30 cycles of 94° C. for 30 seconds, 55° C. for 30 seconds, 72° C. for 1 min and a final extension step at 72° C. for 7 min.

The amplified PCR products were run onto a 2% agarose gel and comprised two major bands of about 850 by corresponding to conventional IgG1 and about 600 by (550-650 bp) corresponding to heavy chain antibodies. The smaller band was cut out of the gel, purified with a QIAquick gel extraction kit (QIAGEN Inc) and re-amplified in a second PCR reaction containing 1 µl of the purified DNA template, 5 pmol each of MJ7, a VH sense primer with a SfiI restriction site, underlined, (5'-CAT GTG TAG ACT CGC GGCCCAGCCGGCCAT GGC C-3'; SEQ ID NO:22) and MJ8, an antisense primer with a SfiI restriction enzyme site, underlined, (5'-CAT GTG TAG ATT CCT GGCCGGCCTGGCCTG AGG AGA CGG TGA CCT GG; SEQ ID NO:23), 5 µl of 10× reaction buffer, 3 µl of 2.5 mM dNTP, 2.5 unit of Taq DNA polymerase (Roche Applied Science, Indianapolis, Ind.) and water to a final volume of 50 µl. The PCR protocol consisted of an initial step at 94° C. for 3 min followed by 30 cycles of 94° C. for 30 seconds, 57° C. for 30 seconds, 72° C. for 1 min and a final extension step at 72° C. for 7 min. The amplified PCR products (about 400-450 bp) that correspond to VHH fragments of heavy chain antibodies were purified with a QIAquick PCR purification kit (QIAGEN Inc.), digested with SfiI (New England BioLabs) and re-purified with the same kit.

EXAMPLE 2

Phage Library Construction and Panning

A phage library containing the DNA isolated in Example 1 was constructed then panned to identify anti-ICAM-1 antibodies. Reactivity of the antibodies was tested using ELISA.

30 µg of pMED1 (Arbabi-Ghahroudi et al., 2009) DNA was digested with SfiI overnight at 50° C. To minimize self-ligation, digestion was continued for additional 2 hours at 37° C. by adding 20 units of both XhoI and PstI restriction enzymes. For library construction, 10 µg of phagemid DNA was ligated with 1.75 µg of VHH fragment DNA (isolated in Example 1) and incubated for 2 hours at RT using the LigaFast DNA ligation system (Promega, Corp., Madison, Wis.), according to the recommended protocol. The ligated product was precipitated with n-butanol, resuspended in sterile water and electroporated into competent E. coli TG1 cells (Stratagene, Cedar Creek, Tex.). Transformed bacterial cells were diluted in SOC medium and incubated for 1 hour at 37° C. with slow shaking. The size of library was calculated by plating aliquots on LB-Amp. The VHH fragments from 30 colonies were PCR-amplified and sequenced for diversity analysis. The library was aliquoted and stored at −80° C.

Panning was performed essentially as described by Arbabi et al. (1997). A 1 ml aliquot of the library ($5 \times 10^{10}$ bacterial cells) was thawed on ice, grown in 300 ml 2×YT with 100 µg/ml ampicillin and 2% glucose for about 2 hours at 37° C. ($OD_{600}$=0.4-0.5). The grown cells were infected with M13KO7 helper phage (New England Biolabs) at a phage to bacteria ratio of 20:1 for 30 min at 37° C. without shaking followed by shaking at 37° C. for one hour. The culture was then centrifuged at 4° C., the infected cell pellets were re-suspended in 300 ml of 2×YT with 100 µg/ml ampicillin and 50 µg/ml kanamycin, and the culture was incubated at 37° C. overnight with vigorous shaking (250 rpm). The phage particles in the culture supernatant were incubated with ⅕ volume of 20% PEG 6000, 2.5 M NaCl, on ice for 1 hour and centrifuged at 10,000 rpm for 15 min. The phage pellets were re-suspended in 2 ml of sterile PBS and titered.

For solid phase panning Maxisorb microtitre plates (Nunc, Roskilde, Denmark) were coated overnight at 4° C. with 50 µg/well of recombinant human ICAM-1. The wells were rinsed once with PBS and blocked with 3% bovine serum albumin (BSA) in PBS for 2 hours at 37° C. Approximately $10^{11}$ library phage were added to the blocked wells, including control wells with no antigen and incubated for 2 hours at 37° C. After 7× washing with PBS containing 0.1% Tween 20, bound phage were eluted with 0.1 M triethylamine, then neutralized and added to exponentially growing TG1 cells. The eluted phage were titered and the infected bacterial cells were super-infected with M13KO7 and grown overnight at 37° C. Panning was continued for three more rounds following the same procedure except that the amount of coated ICAM-1 antigen was reduced to 40, 30, and 20 µg for the second, third and fourth rounds, respectively. Colony-PCR was performed on twenty-four individual colonies randomly picked after the last round of panning and the sequences of amplified VHH genes were determined.

Figure 1:
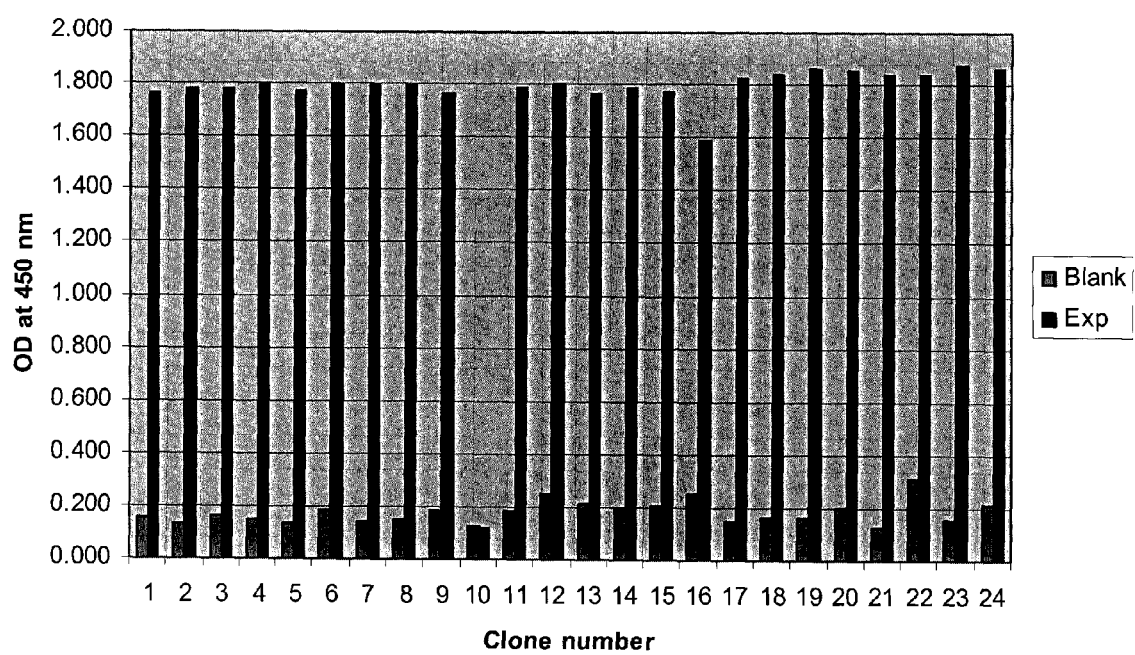
FIG. 1 is a bar graph showing the absorbance readings of ICAM-1 phage ELISA. Phage ELISA experiment was performed on individual clones. Phage supernatants from individual colonies were added to ICAM-1-coated wells. After washing the wells, bound phage were detected with anti-M13-HRP conjugate and addition of KPL peroxidase substrate. The absorbance were read at 450 nm.

For phage-ELISA, the positive clones were grown to $OD_{600}$=0.3-0.4 in 2×YT containing 100 µg/ml ampicillin and 0.1% glucose, then infected by M13KO7 helper phage. The cultures were grown at 37° C. overnight. Phage supernatants were then collected by centrifugation and their reactivity was measured by phage ELISA. Briefly, ELISA wells were coated overnight at 4° C. with 5 µg/ml of the recombinant ICAM-1 and blocked with 3% BSA for additional 2 hours at 37° C. Phage supernatants were added to the wells and incubated for 2 hours at 37° C. The presence of phage binding was detected by an anti-M13/HRP conjugate (GE Healthcare, Mississauga, ON). After 1 hour at room temperature, KPL peroxidase substrate (KPL, Gaithersburg, Md.) was added. Color development was stopped by adding 100 µl 1M phosphoric acid and the plates were read at 450 nm. Results are shown in FIG. 1.

EXAMPLE 3

Expression of Soluble sdAb $V_HH$ antibodies isolated via phage panning in Example 2 and showing reactivity to ICAM-1 were expressed and their reactivity confirmed via ELISA.

DNA corresponding to the $V_HH$ antibodies identified in Example 2 was inserted into an expression vector. Restriction enzyme sites BbsI and BamHI were added to the 5' and 3' ends of the positive $V_HH$ DNA fragments via a PCR using gene-specific sense primer VHH BbsI (5'-TATGAAGACACCAG-GCCCAGGTGCAGCTGGTGGAGTCT-3'; SEQ ID NO:24) and anti-sense primer VHH-BamHI (5'-CGCGGGATCCT-GAGGAGACGGTGACCTGGGT-3'; SEQ ID NO:25). The amplified DNA was then digested with BbsI and BamHI restriction enzymes and ligated into digested pSJF2 vector using standard techniques (Tanha et al., 2003). Competent E. coli TG1 cells were transformed with the vectors and clones expressing anti-ICAM-1-specific recombinant VHH were grown in 1-liter cultures of 2×YT medium+ampicillin (100 mg·mL−1) with 0.1% glucose to an $OD_{600}$ of 0.8. Cultures were induced with 1 mM IPTG and grown overnight on a rotary shaker at 28° C.

After confirmation of expression by SDS-PAGE and Western blotting, recombinant $V_HH$ proteins were extracted from the bacterial cells by standard lysis methods, purified by immobilized metal affinity chromatography (IMAC), and quantified as described elsewhere (Tanha et al. 2001). The state of aggregation of the purified protein was determined by size exclusion chromatography on Superdex 200 (Amersham Biosciences). The reactivity of the individual VHH proteins was confirmed by ELISA, in which rabbit anti-His6 antibody conjugated to HRP was used for the detection of binding.

FIGS. 2 to 4 show nucleotide and amino acid sequences of single-domain antibody clones 11-4, 5-5 and 34-1, respectively. These clones were reactive with intracellular adhesion molecule 1 (ICAM-1).

Figure 5:
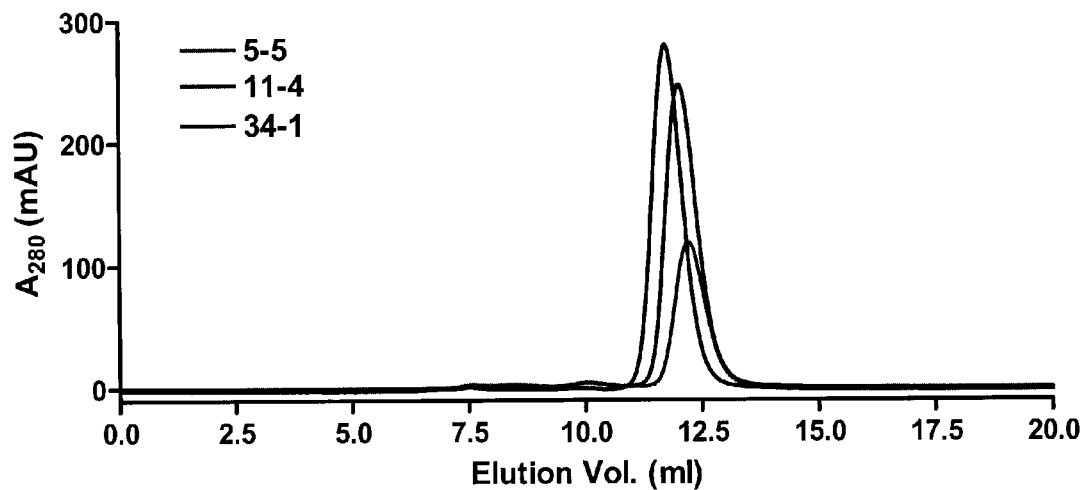
FIG. 5 shows a size-exclusion chromatogram of anti-ICAM-1 sdAb clones 11-4, 5-5, and 34-1. All expressed and purified clones were shown to be monomeric.
Figure 6:
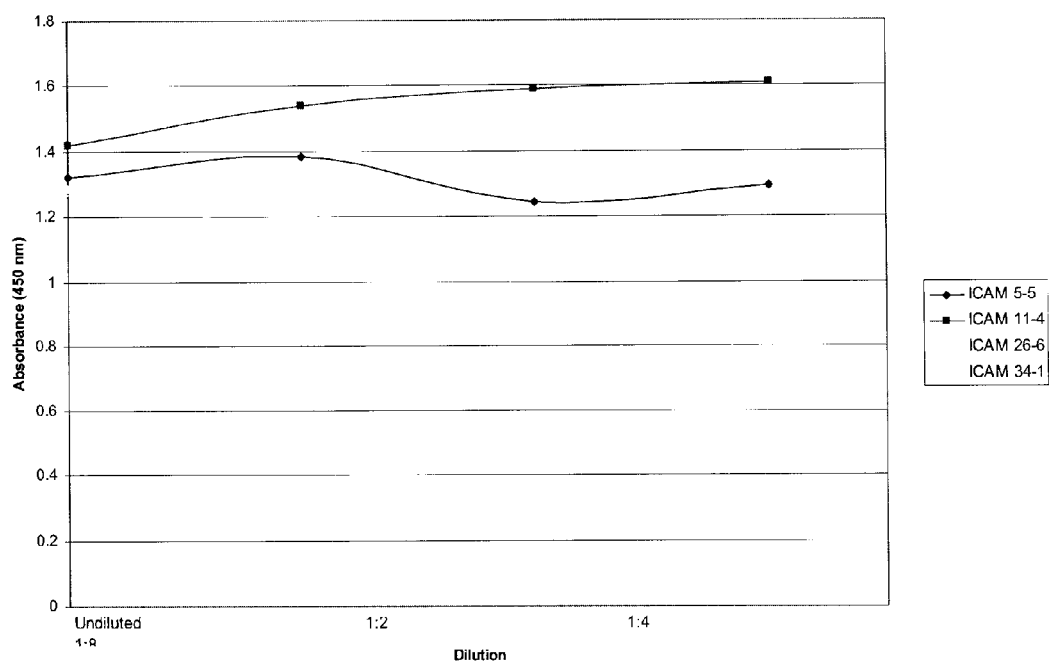
FIG. 6 is a graphical representation of ICAM-1 binding of purified anti-ICAM-1 sdAb clones 5-5, 26-6, 11-4, and 34-1 determined by ELISA. Anti-histidine tag-HRP antibodies were used to detect the sdAb bound to recombinant ICAM-1 protein.

Size exclusion chromatography employing Superdex™ 75 was used to assess the aggregation state of $V_HH$ domains. Non-aggregating $V_H$s should yield chromatograms with a single, symmetrical peak in elution volumes expected for a monomeric $V_H$. Briefly, a Superdex™ 75 (Superdex 75 10/300, GE Healthcare Cat. No 17-5174-01, ID No 0651148) size exclusion column was washed with 50 mL of filtered and degassed ddH$_2$O and subsequently equilibrated with 50 mL of running buffer, HBS-EP (10 mM HEPES, pH 7.4, 150 mM NaCl, 3 mM EDTA, 0.005% surfactant P20), at a pump speed of 0.5 mL/min. 200 μL of purified $V_H$ (≥1 mg/mL) was injected and eluted, and obtain a chromatogram was obtained. The monomeric and aggregate peaks were integrated to obtain % monomer. Size-exclusion chromatography (FIG. 5) of these purified sdAb clones showed them to be monomeric Additionally, ELISA experiment on individual clones was performed to assess binding of $V_HH$ to the recombinant human ICAM-1. Briefly, Maxisorp™ microtiter plates (Nunc) were coated with 100 μl of 5 μg/ml of the recombinant ICAM-1 (R&D Systems, Inc., Minneapolis, Minn. 55413, USA) in PBS overnight at 4° C. After blocking with 3% bovine serum albumin (300 μl) for 2 h at RT and subsequent removal of blocking agent, 100 μL His$_6$-tagged VH$_H$ at concentrations of a few μM were added, followed by incubation for 2 h at 37° C. Wells were washed 5× with PBST, and 100 μl rabbit anti-His-IgG/horse radish peroxidase (HRP) conjugate (Bethyl Laboratories, Inc., Montgomery, Tex.) was added at a dilution of 1:5000. The wells were then incubated for 1 h at 37° C. After washing the wells with PBST, 100 μL ABTS substrate (KPL, Gaithersburg, Md.) was added and the reaction, seen as color development, was stopped after 5 min by adding 100 μL of 1M phosphoric acid. Absorbance values were measured at a wavelength of 405 nm using a microtiter plate reader. Assays were performed in duplicates. The ELISA assays on individual clones 5-5, 26-6, 11-4, and 34-1 (FIG. 6) showed them to positively react with ICAM-1.

EXAMPLE 4

SPR Analysis of $V_HH$

Surface plasmon resonance (SPR) assays were conducted on the purified $V_HH$ of Example 4 to determine the binding affinity of individual clones to ICAM-1.

Three clones (5-5, 11-4, and 34-1) obtained in Example 4 were individually passed through size exclusion columns, Superdex 75 (GE Healthcare) in 10 mM HEPES, pH 7.4, containing 150 mM NaCl, 3 mM EDTA; monomeric sdAb fractions were collected and protein concentrations were determined by measuring A$_{280}$. SPR analyses were performed with Biacore 3000 instrument (GE Healthcare). All measurements were carried out at 25° C. in 10 mM HEPES, pH 7.4, containing 150 mM NaCl, 3 mM EDTA and 0.005% surfactant P20 (GE Healthcare). Approximately 700-900 RUs of the recombinant ICAM-1 was captured on SA sensor chip (GE Healthcare) at a flow rate of 5 μl/min. Various concentration of the monomeric $V_HH$ were injected over the ICAM-1 surface, using a SA surface as a reference, at a flow rate of 40 μl/min. Surfaces were generated by washing with running buffer. Data were analysed with BIAevaluation 4.1 software.

Figure 7:
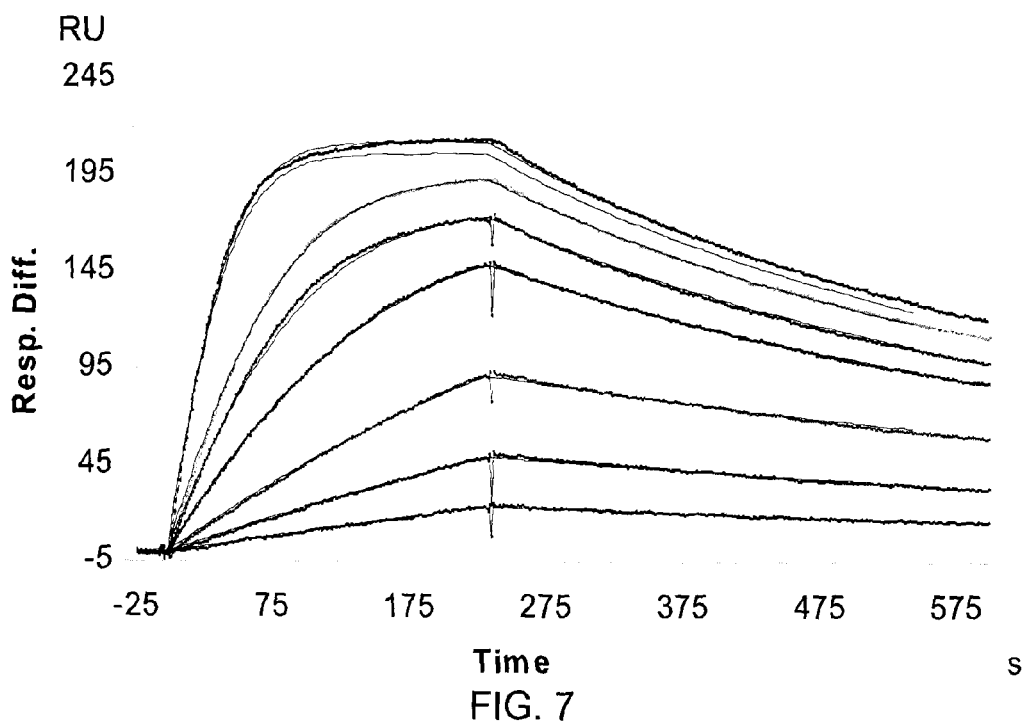
FIG. 7 shows a surface plasmon resonance (SPR) sensorgram depicting the binding of llama sdAb clone 11-4 to recombinant human ICAM-1.
Figure 8:
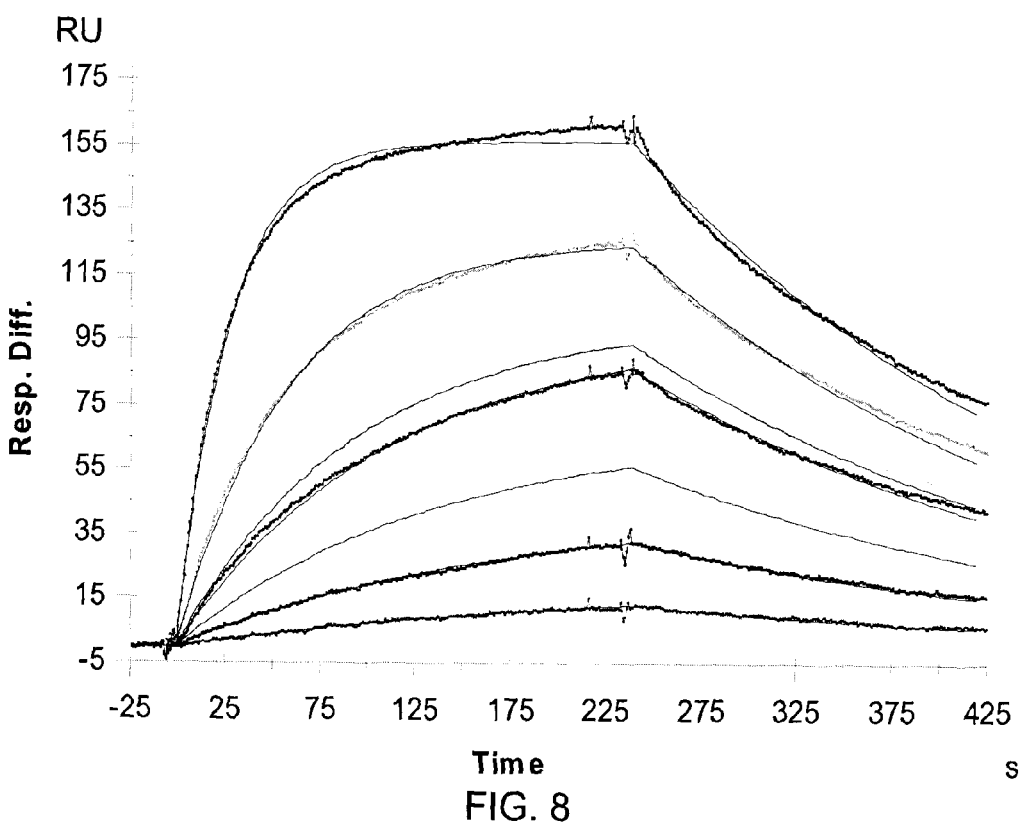
FIG. 8 shows a SPR sensorgram depicting the binding of llama sdAb clone 5-5 to recombinant human ICAM-1.
Figure 9:
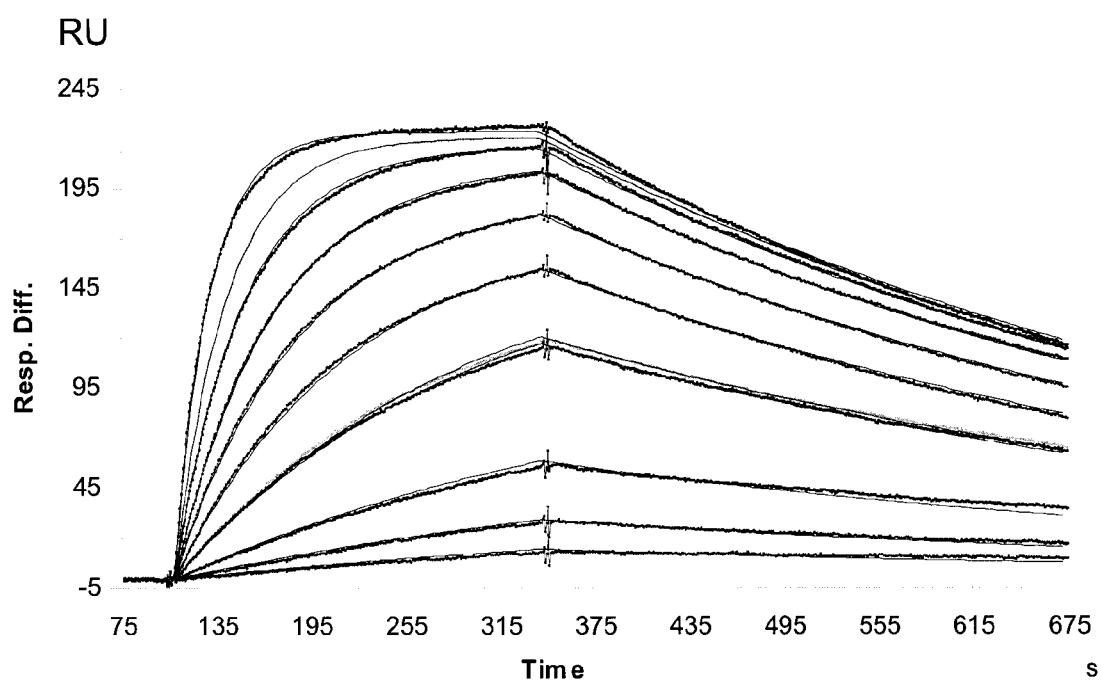
FIG. 9 shows a SPR sensorgram depicting the binding of llama sdAb clone 34-1 to recombinant human ICAM-1.

SPR analysis of binding of sdAb clones 11-4, 5-5, and 34-1 to recombinant human ICAM-1 are shown in FIGS. 7, 8, and 9, respectively. Table 1 shows the binding affinities (Kd, Ka, K$_D$) for clones 11-4, 5-5 and 34-1. It provides a summary of affinities for the representative antibodies of the invention, as determined by surface plasmon resonance (Biacore).

TABLE 1

| Biding affinities of clones 11-4, 5-5, and 34-1. | | | |
|---|---|---|---|
| ICAM-1 binder | KD (M) | kd (s-1) | ka (M-1s-1) |
| 5-5 | $6 \times 10^{-8}$ | $4 \times 10^{-3}$ | $7 \times 10^{4}$ |
| 11-4 | $9 \times 10^{-10}$ | $2 \times 10^{-3}$ | $2 \times 10^{6}$ |
| 34-1 | $1 \times 10^{-8}$ | $2 \times 10^{-3}$ | $1 \times 10^{5}$ |

EXAMPLE 5

Immunofluorescence of Anti-ICAM-1 Single-Domain Antibodies in Rat Brain Endothelial Cells The purified $V_HH$ of Example 4 was tested to validate its activity and to determining whether the antibody can detect inflammation.

Rat brain endothelial cells (SV-RBEC) were cultured on coverslips for 3 days in DMEM and 10% FBS. ICAM-1 expression was induced by adding 5 μg (1 mg/ml) of lipopolysaccharide (LPS; Sigma) overnight. Cells were then washed 3× with cold PBS, fixed with 3.7% formaldehyde for 20 min, washed again 3× in PBS at RT, and then blocked with 5% of normal goat serum/PBS for 1 h at RT. 25 μg anti-ICAM-1 IgG or 50 μg anti-ICAM-1 single domain antibodies (34-1, 11-4, 5-5) labelled with Cy5.5 (red) were incubated for 1 h at RT then washed 3× in PBS. The washed cells were incubated in 1:500 WGA-FITC/PBS for 1 min on ice, for membrane staining (green) then washed again 3× with PBS. Coverslips were then mounted in DAKO mounting medium containing 2 μg/ml of Hoechst for nuclear staining (blue).

Figure 10:
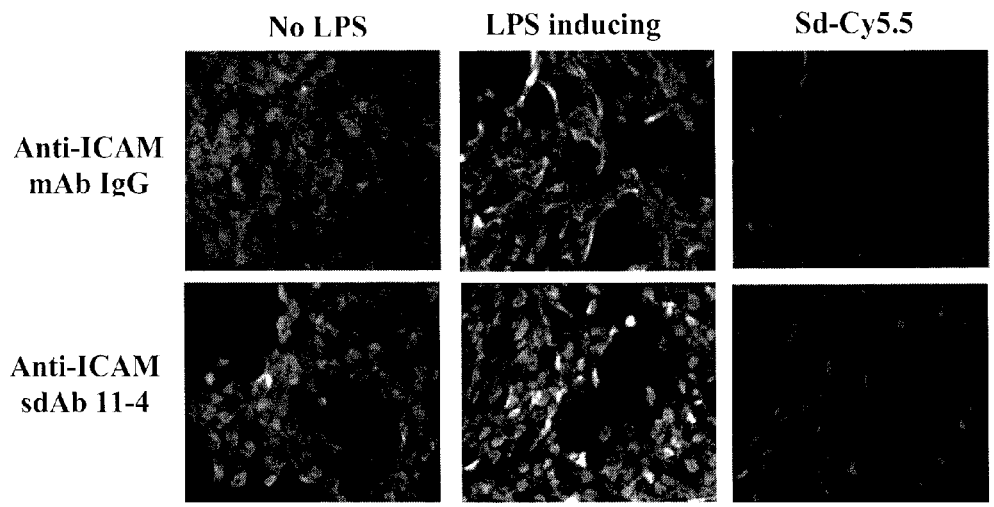
FIG. 10 shows ICAM-1 immunofluorescence detected with anti-ICAM-1 sdAb clone 11-4 labelled with Cy5.5 or Cy5.5-labelled anti-ICAM-1 IgG mAb (as a reference antibody) in rat brain endothelial cells exposed or not to lipopolysacchardies (LPS) to induce inflammation
Figure 11:
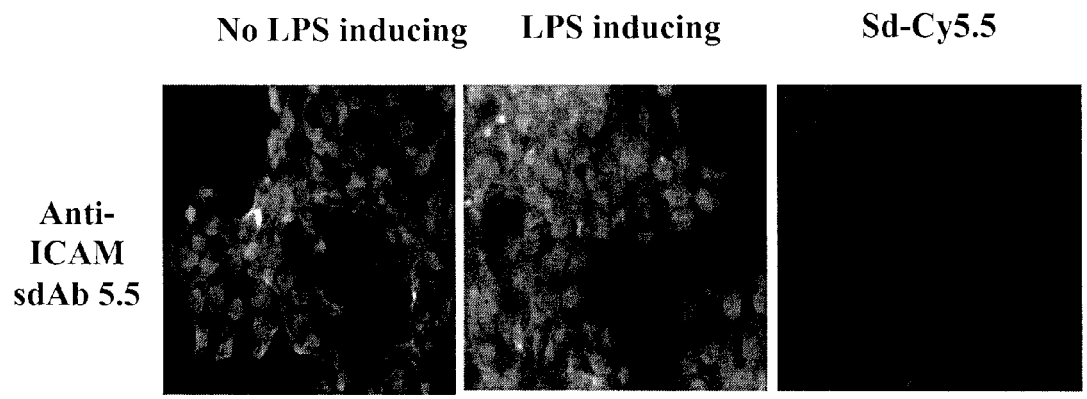
FIG. 11 shows ICAM-1 immunofluorescence detected with anti-ICAM-1 sdAb clone 5-5 labelled with Cy5.5 in rat brain endothelial cells exposed or not to lipopolysacchardies (LPS) to induce inflammation
Figure 12:
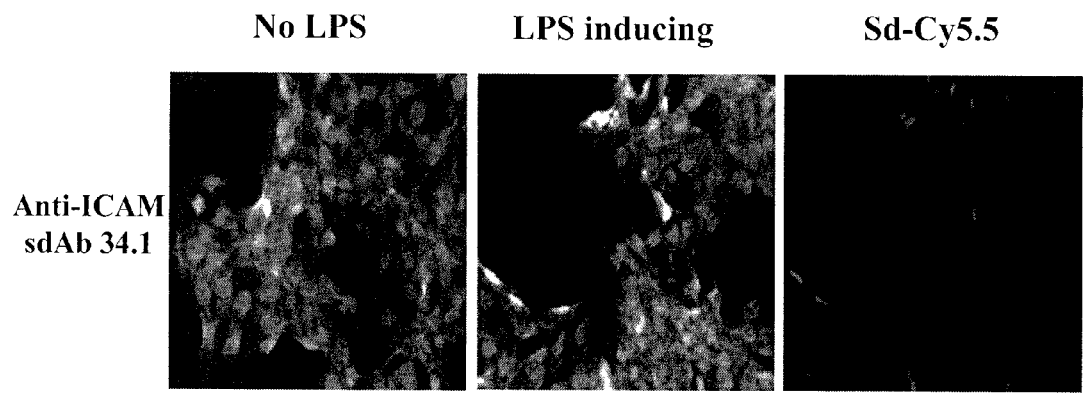
FIG. 12 shows ICAM-1 immunofluorescence detected with anti-ICAM-1 sdAb clone 34-1 labelled with Cy5.5 in rat brain endothelial cells exposed or not to lipopolysacchardies (LPS) to induce inflammation

Results of the ICAM-1 immunofluorescence assay are shown in FIGS. 10 to 12. Results show that the anti-ICAM-1 sdAb can detect ICAM-1 as a marker for LPS-induced inflammation in rat brain endothelial cells.

EXAMPLE 6

Mouse Model of Atherosclerosis

Rodents do not develop atherosclerosis spontaneously. For this reason the apolipoprotein E knockout (apoE KO) mouse model was used to study ability of anti-ICAM-1 sdAb to detect atherosclerotic plaques. Apolipoprotein E is a ligand for receptors that clear remnants of chylomicrons and very low density lipoproteins. ApoE KO mice develop atheromas in large arteries, including aorta and carotid arteries; these histologically resemble those found in humans (Weinreb et al 2007). Although these mice develop atheromas spontaneously, the rate of plaque formation is enhanced when they are fed a high fat diet for a period of 3 to 9 months. For the present experiments, mice were fed a high fat diet for a period of 4 months, starting at 2 months of age.

To confirm that ApoE knockout animals develop atherosclerotic plaques on high-fat diet and that these plaques exhibit up-regulated expression of ICAM-1, the animals were sacrificed after four moths of high-fat diet and their aortas were dissected, sectioned and evaluated by immunofluorescence staining against ICAM-1 using a commercial anti-ICAM monoclonal antibody.

Briefly, sample slides of 12 µm saline-perfused, not fixed, frozen aortic sections of ApoE KO mice and C57B control (Ctrl) mice were prepared. Samples were fixed with 100% MeOH 10 min at RT, washed with 3×1×PBS, then rinsed with MilliQ $H_2O$ (to wash off any OCT tissue tek embedding medium from the slides) followed with 3×1×PBS. Slides were then blocked with 10% Normal Goat Serum (NGS) (Cat# G6767, Sigma)+0.01% TritonX-100 in 1×PBS for 1 h at RT. To stain endothelial cells, rat anti-mouse CD31 (Cat#557355, BD Pharmingen) was incubated at a dilution of 1:300 in 5% NGS in 1×PBS for 1 h at RT, then rinsed with 3×1×PBS. Secondary antibody Goat anti-rat Alexa568 (Cat# A-11077, Invitrogen) was then incubated at 1:500 in 1×PBS for 1 h at RT, and rinsed with 3×1×PBS. Armenian hamster anti-ICAM-1 1 mg/mL (Cat#553249, BD Pharmingen) 1:250 in 5% NGS in 1×PBS was incubated for 1 h at RT to detect ICAM-1 expression and then rinsed with 3×1×PBS. Secondary antibody goat-anti-armenian hamster Alexa488 (Cat# sc-2446 Santa Cruz) 1:300 in 1×PBS-1 h at RT was used afterward. Cover slipped in Dako fluorescent mounting medium (Cat# S3023, Dako) spiked with Hoechst (1 µg/mL) (Cat# H3570, Invitrogen). Images were acquired using Olympus IX81 Fluorescent Microscope and InVivo program. Images were corrected for background noise using ImagePro v6.2 and AxioVision LE rel4.4 software.

Figure 13:
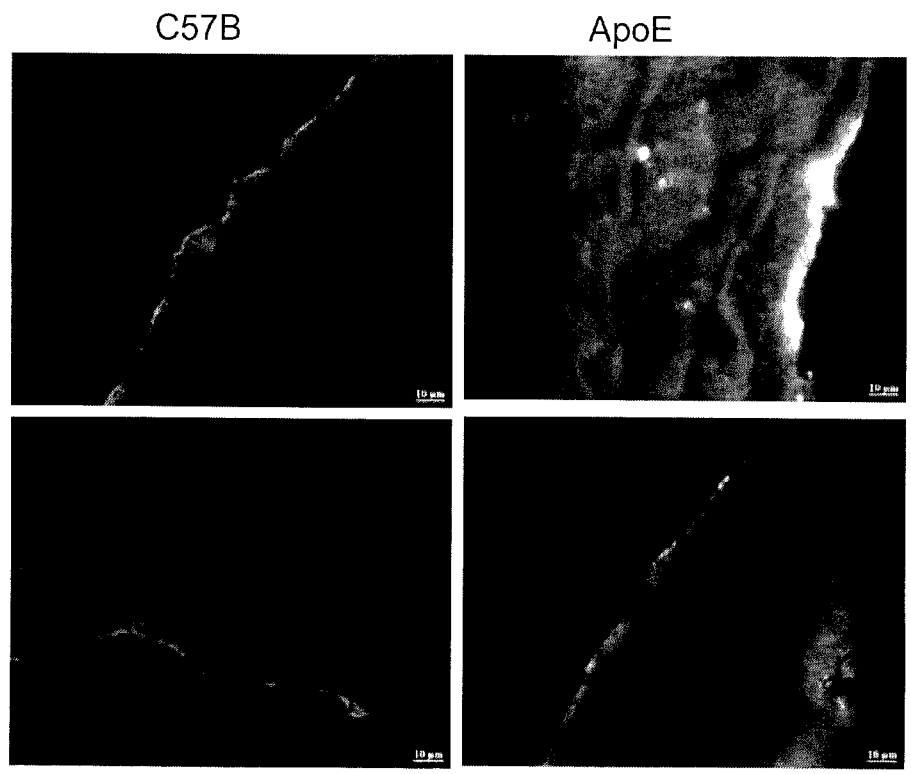
FIG. 13 shows images of immunofluorescence of ICAM-1 in aortic sections from ApoE KO and C57B Ctrl mice. Data validates the expression of ICAM-1 in ApoE KO mice after 4 months of high fat diet. The images show that in the animal models used for in vivo imaging (i.e., ApoE-knockout), ICAM-1 is indeed up-regulated in aorta using immunochemistry detection with monoclonal anti-ICAM-1 antibody in isolated aorta.

Results show up-regulated expression of ICAM-1 in endothelial layer of aortas from ApoE knockout animals fed high-fat diet for 4 months compared to control animals (FIG. 13). Plaque formation in this model was further monitored monthly by non-invasive in vivo imaging using anti-ICAM-1 single domain antibodies (see Example 7). C57Bl/6 mice on a high fat diet were used as wild type (WT) controls.

EXAMPLE 7

In Vivo Near-Infrared Fluorescence Imaging of APO E Knockout Mice

The antibodies of Example 4 were labelled with fluorescent agent and were used for non-invasive optical imaging of ApoKO and control mice (of Example 6).

Anti-ICAM-1 antibodies were labelled with Cy5.5 succimidyl ester using methods recommended by the manufacturer (GE Healthcare). Labelling was optimized such that each sdAb had a dye/antibody ratio of two. The presence of plaques in the aorta of atherosclerotic mice (Example 6) was visualized monthly via tail vein injection of 50 µg of anti-ICAM-1 sdAb using non-invasive in vivo optical imaging. In vivo imaging studies were performed using a small-animal time-domain eXplore Optix MX2 pre-clinical imager (Advanced Research Technologies, Montreal, QC) at 4, 24, 48, and 72 h after injection. For imaging, mice were first anesthetized with isofluorane, and then positioned on an animal stage in a chamber that allows for maintenance of gaseous anesthesia. A pre-injection scan was routinely performed to determine baseline fluorescence level. At the end of the study, animals were euthanized and perfused, organs were removed and imaged. In all imaging experiments, a 670-nm pulsed laser diode with a repetition frequency of 80 MHz and a time resolution of 12 ps light pulse was used for excitation. The fluorescence emission at 700 nm was collected by a highly sensitive time-correlated single photon counting system and detected through a fast photomultiplier tube. The data were recorded as temporal point-spread functions (TPSF) and the images were reconstructed as fluorescence concentration maps using ART Optix Optiview analysis software 2.0 (Advanced Research Technologies, Montreal, QC).

Figure 14:
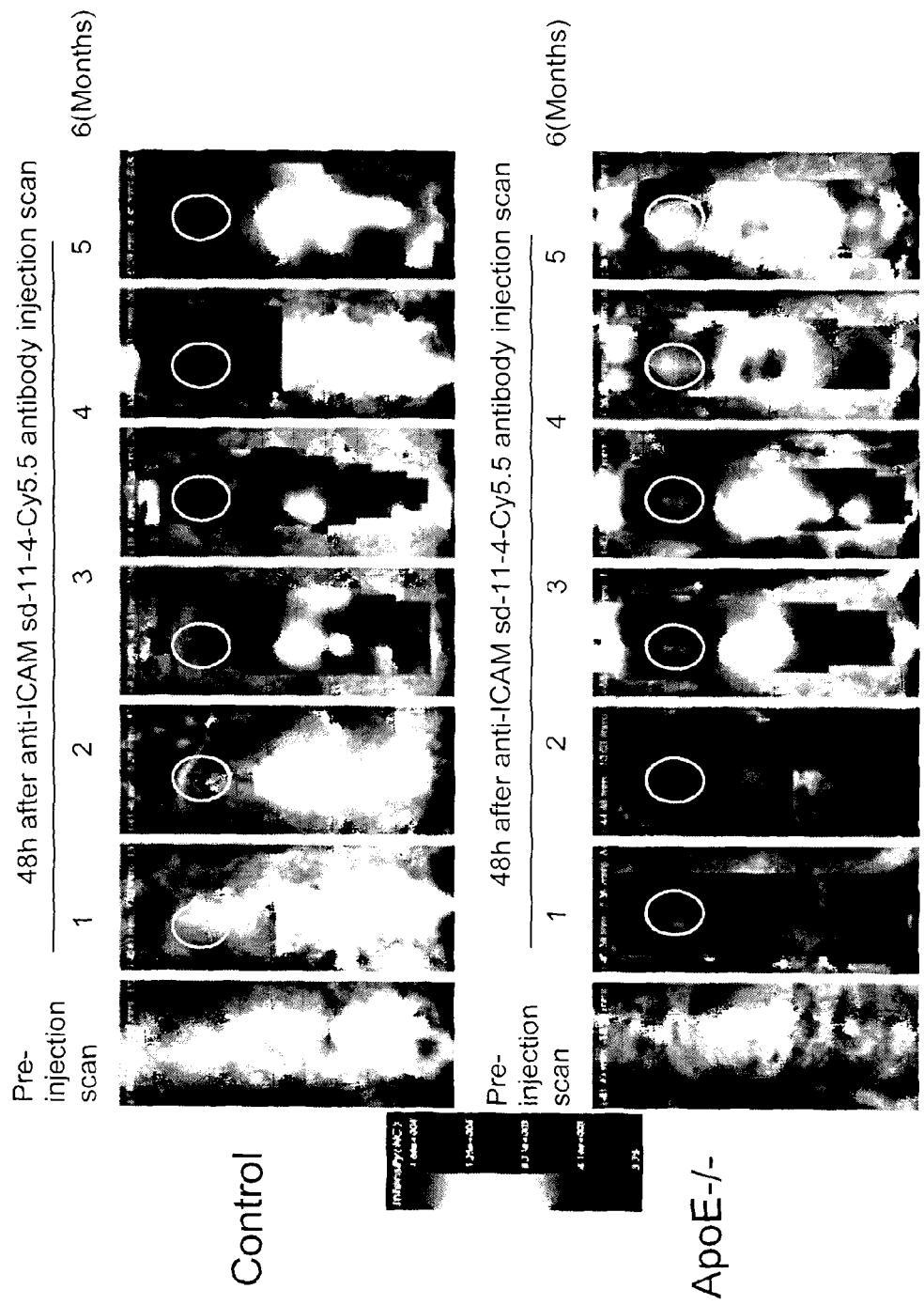
FIG. 14 shows images of longitudinal non-invasive in vivo imaging of ICAM-1 using anti-ICAM-1 sdAb 11-4 in ApoE KO and control mice. The mice were injected with 50 μg anti-ICAM-1 sdAb 11-4 labelled with Cy5.5, 48 h prior to imaging at indicated time points after starting high-fat diet. Data indicates that ApoE KO mice have high intensity signal in aortic region compared to control mice from 1 month to 6 months after start of a high fat diet.
Figure 15:
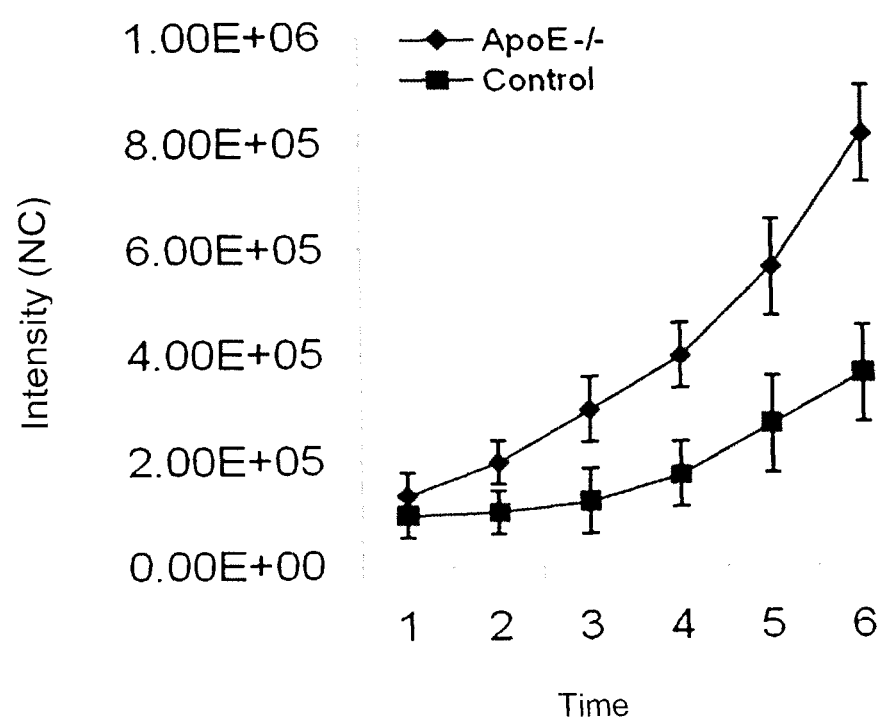
FIG. 15 is a graph showing quantification of ICAM-1 signal in ApoE KO and control mice after longitudinal non-invasive in vivo imaging using anti-ICAM-1 sdAb 11-4. Each point is mean+/−SD of image intensity signal in aortic region (ROI) in four animals imaged as described in FIG. 14.
Figure 17:
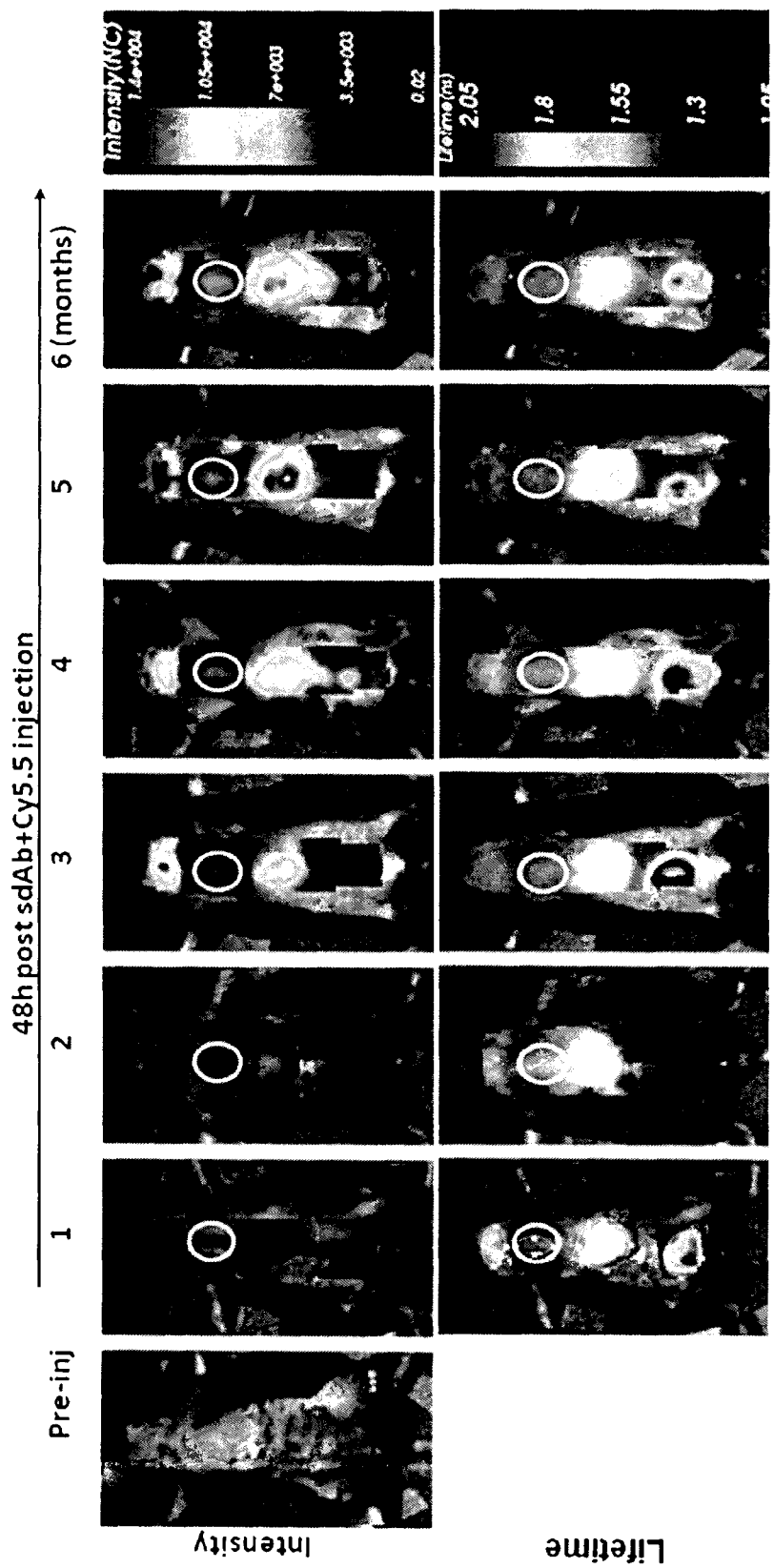
FIG. 17 shows fluorescence Intensity and fluorescence lifetime map images of ApoE −/− mice. The image shows different fluorescent lifetime values for the injected anti-ICAM-1 sdAb-Cy5.5 in different regions of the body (bladder, liver, and heart). Circles highlight high fluorescence intensity in the aorta/heart region.
Figure 18:
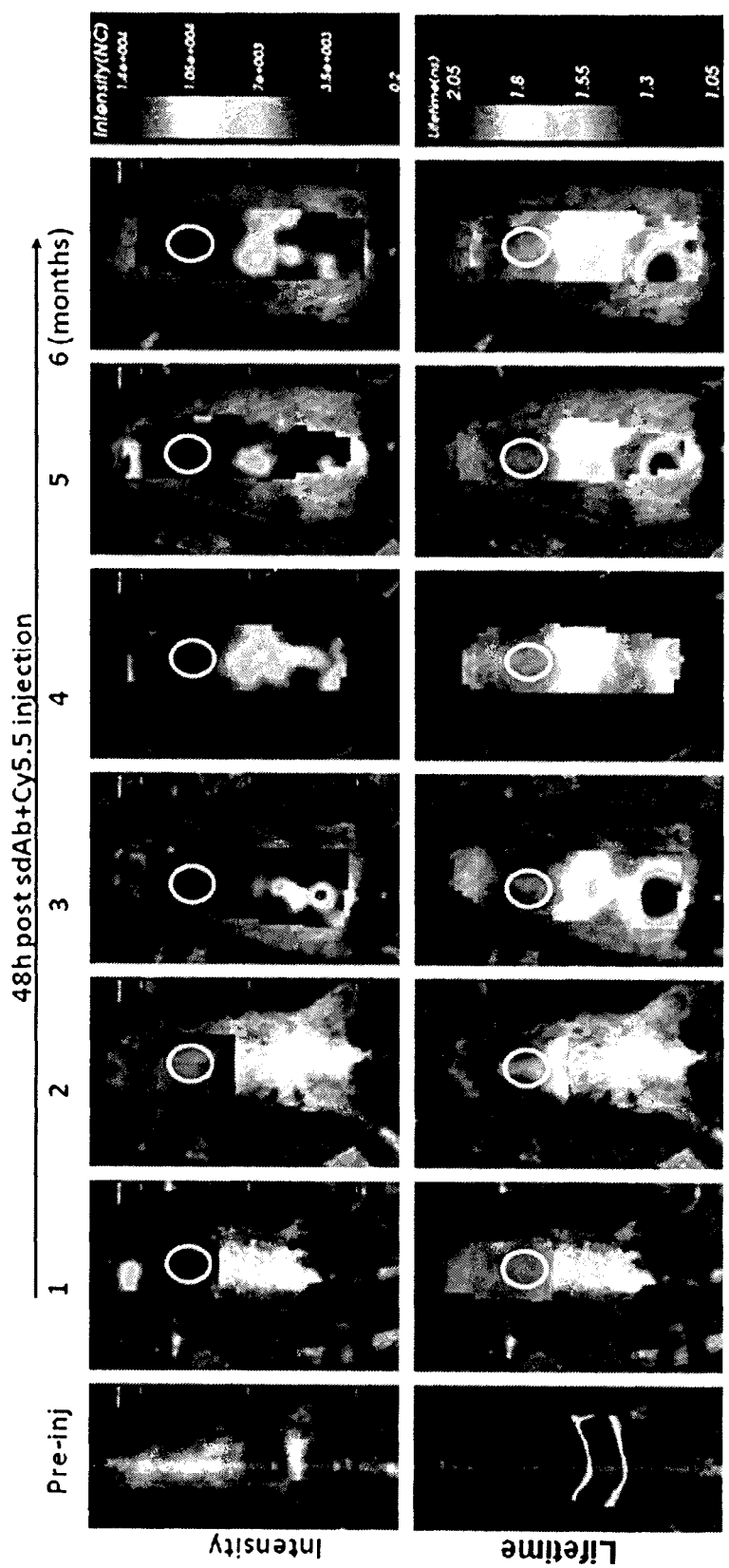
FIG. 18 shows fluorescence intensity and fluorescence lifetime map images of control mice. The image shows different fluorescent lifetime values for the injected anti-ICAM-1 sdAb-Cy5.5 in different regions of the body. No fluorescence intensity was observed in the aorta/heart region (circled).
Figure 19:
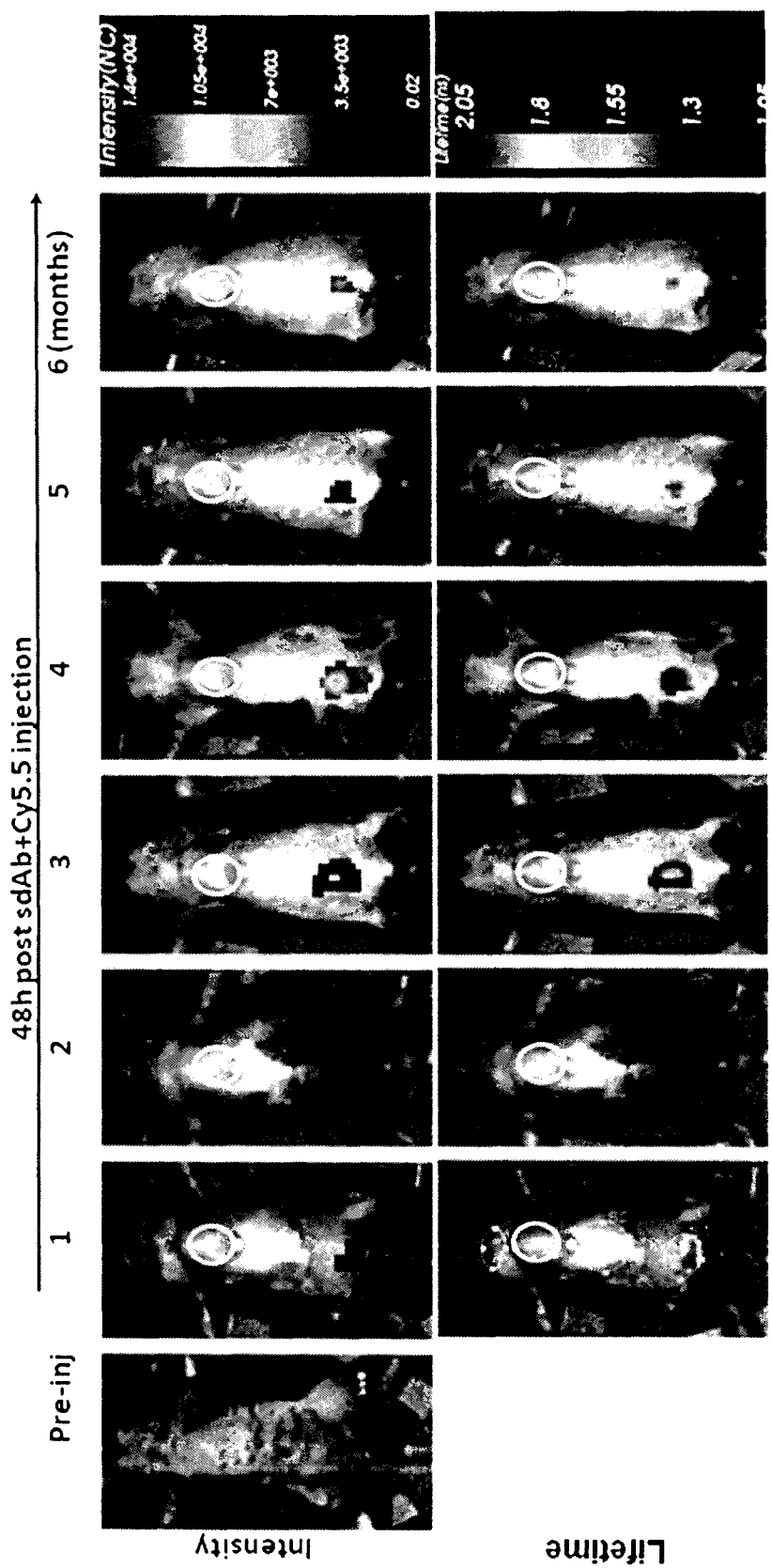
FIG. 19 shows gated fluorescence intensity and fluorescence lifetime images in ApoE −/− mice. When using time-domain imaging and lifetime gating between (1.05-1.65 ns), most of the fluorescent signal is in the bladder region, which can be attributed to free Cy5.5 fluorophore that has lifetime between 1 and 1.3 ns. The heart/aortic region is circled.
Figure 20:
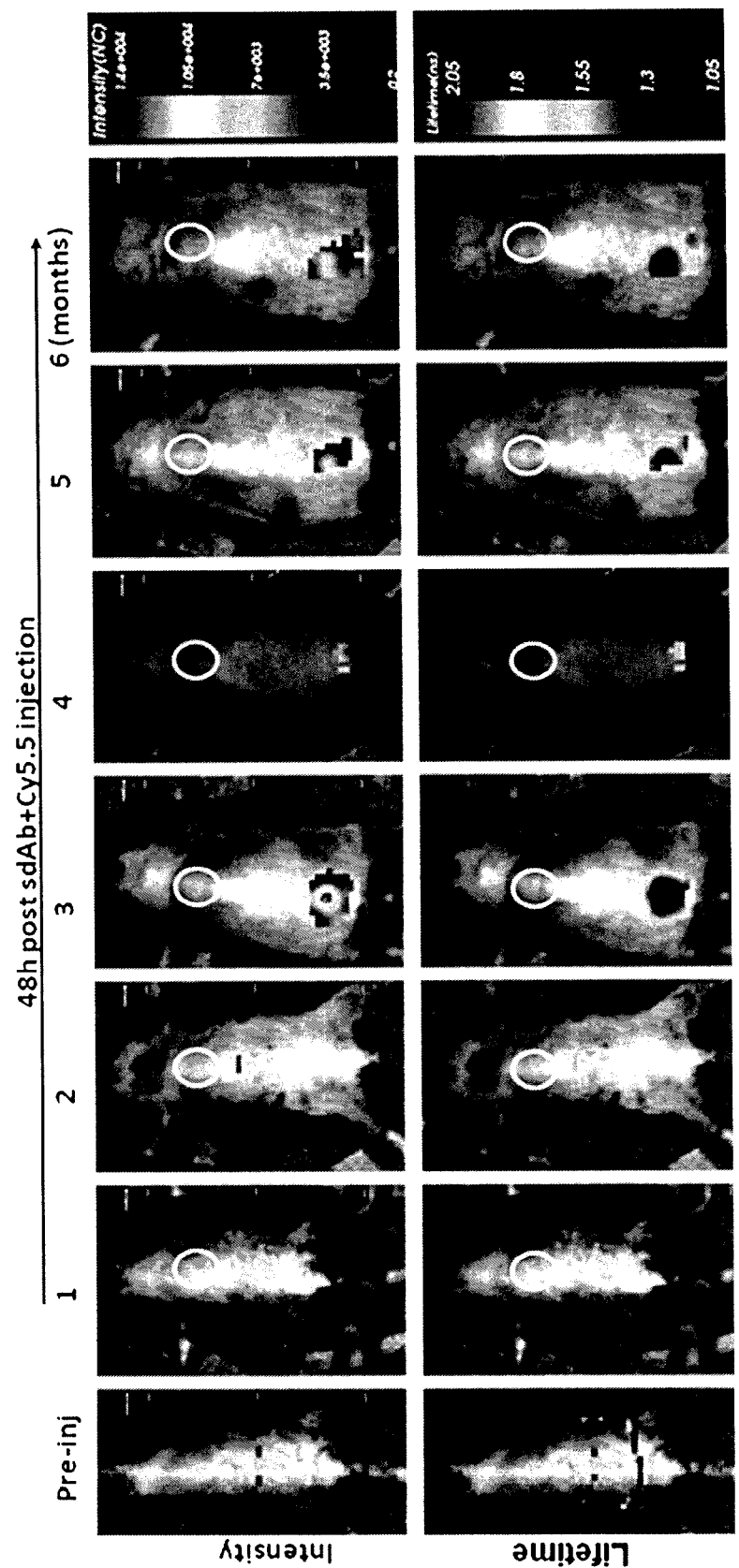
FIG. 20 shows gated fluorescence intensity and fluorescence lifetime images of control mice. When using time-domain and lifetime gating between (1.05-1.65 ns), most of the fluorescent signal is in the bladder region and can be attributed to free Cy5.5 fluorophore, which has lifetime between 1 and 1.3 ns. The heart/aortic region is circled.

Results are presented in FIGS. 14 to 25. FIG. 14, the longitudinal near-infrared optical imaging of atherosclerotic plaques in the aortic artery, shows that the fluorescent signal is more intense in the aortic region of the ApoE KO mice compared to control mice. These findings were quantified and shown in FIG. 15, supporting higher levels and faster progression of the ICAM-1 signal in aortic region of interest (ROI) in ApoE-knockout animals compared to control animals fed high-fat diet. FIG. 16 shows a high optical signal in the heart/aortic region of ApoE KO mice and confirms that the fluorescent signal originated from the heart and aortic tissues using three-dimensional reconstruction of images. FIG. 17 shows that the fluorescent signal after injecting anti-ICAM-1 sdAb-Cy5.5 was detected in the liver, heart, and bladder region of the ApoE −/− mice, compared to control mice (FIG. 18), where the signal was lacking in the heart region.

Figure 21:
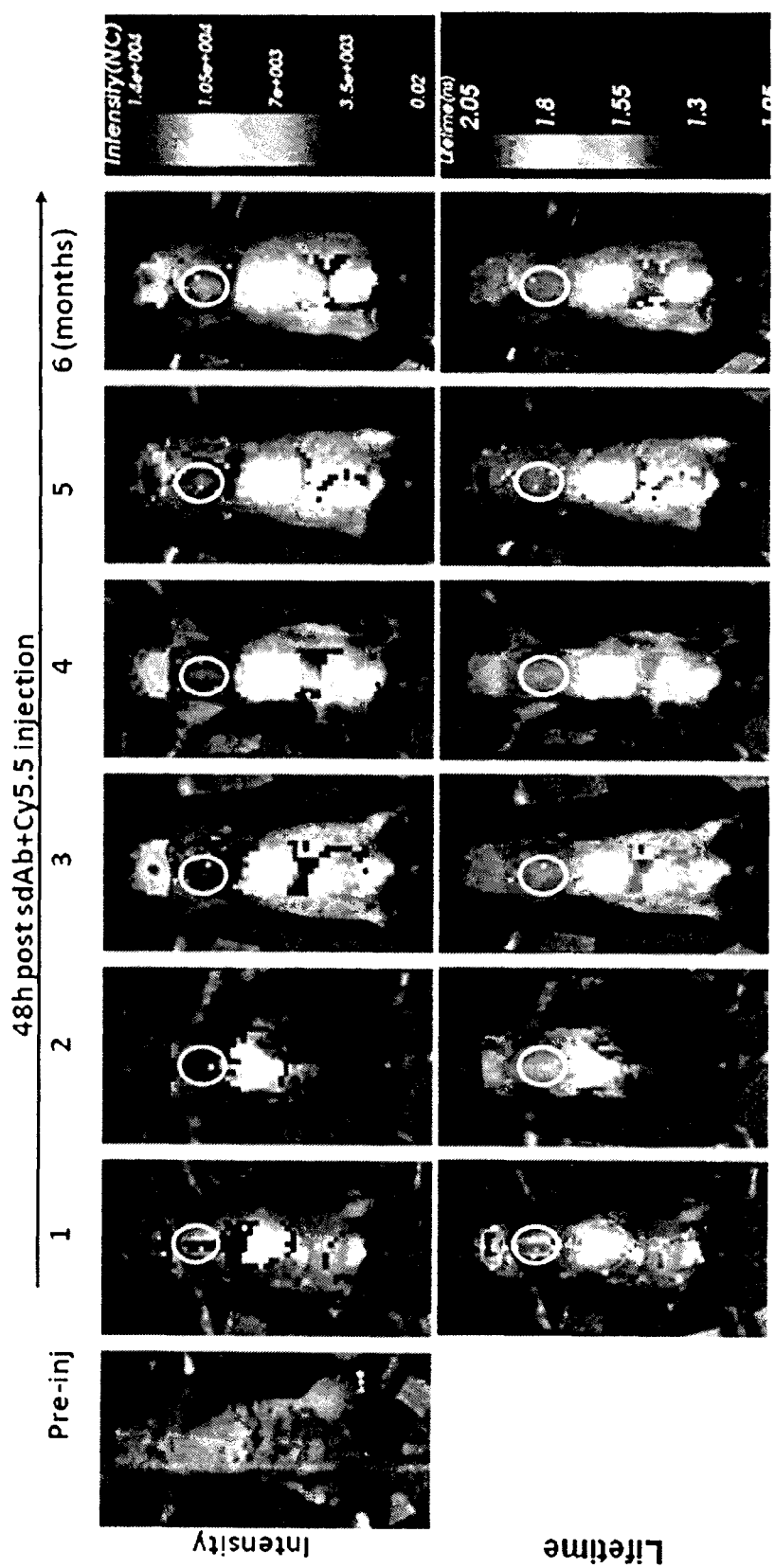
FIG. 21 shows gated fluorescence intensity and fluorescence lifetime images in ApoE −/− mice. When using time-domain optical imaging and lifetime gating between (1.85-1.95 ns), most of the fluorescent signal is in the heart/aortic region. This fluorescent signal is attributed to anti-ICAM-1 sdAb-Cy5.5 conjugate bound to atherosclerotic plaques. Anti-ICAM-1 sdAb-Cy5.5 conjugate has longer fluorescence life time than free Cy5.5 (1-1.3 ns). The heart/aortic region is circled.
Figure 22:
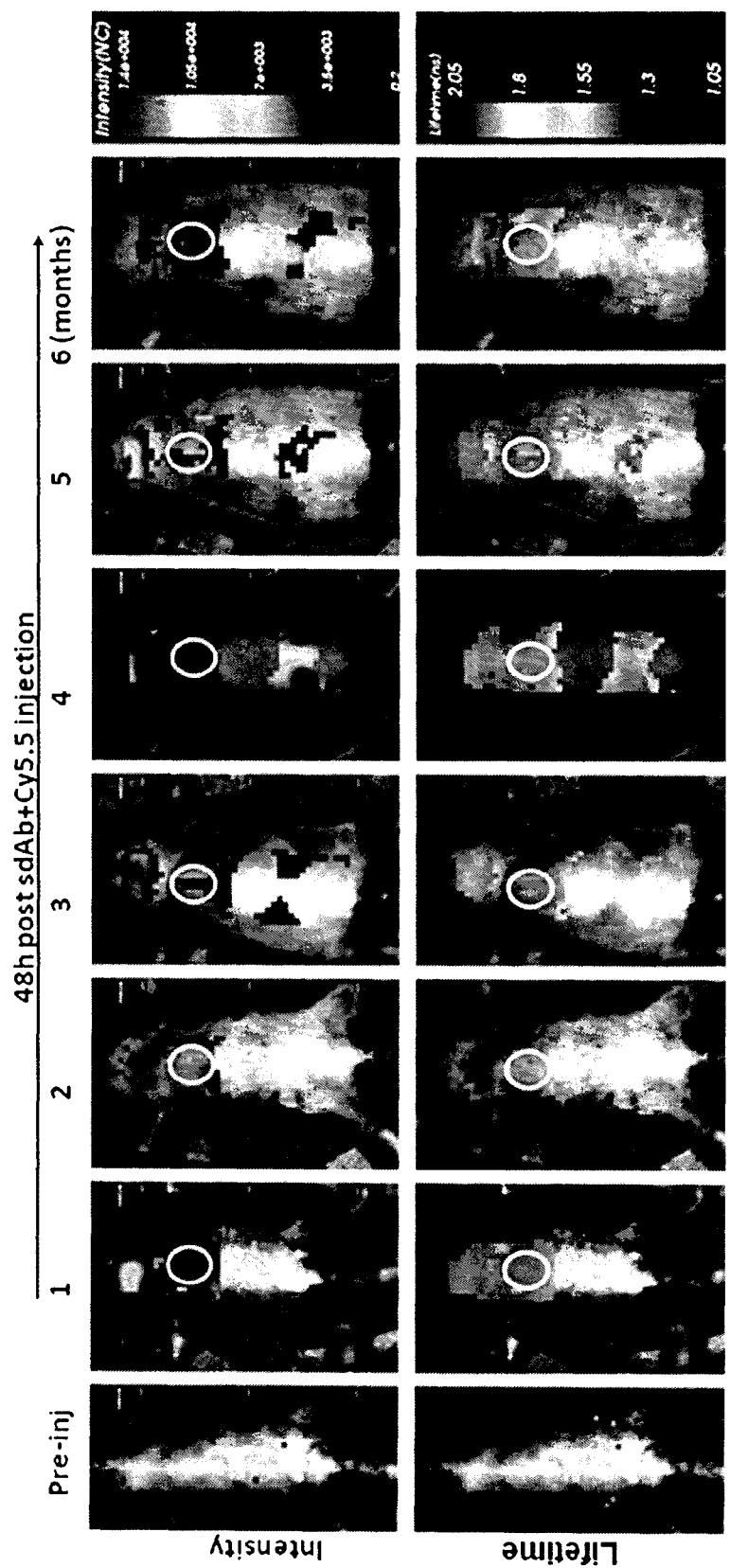
FIG. 22 shows gated fluorescence intensity and fluorescence lifetime images of control mice. When using time-domain optical imaging and lifetime gating between (1.85-1.95 ns). Anti-ICAM-1sdAb-Cy5.5 conjugate has longer fluorescence life time than that of free Cy5.5 (1-1.3 ns). The heart/aortic region is circled.
Figure 23:
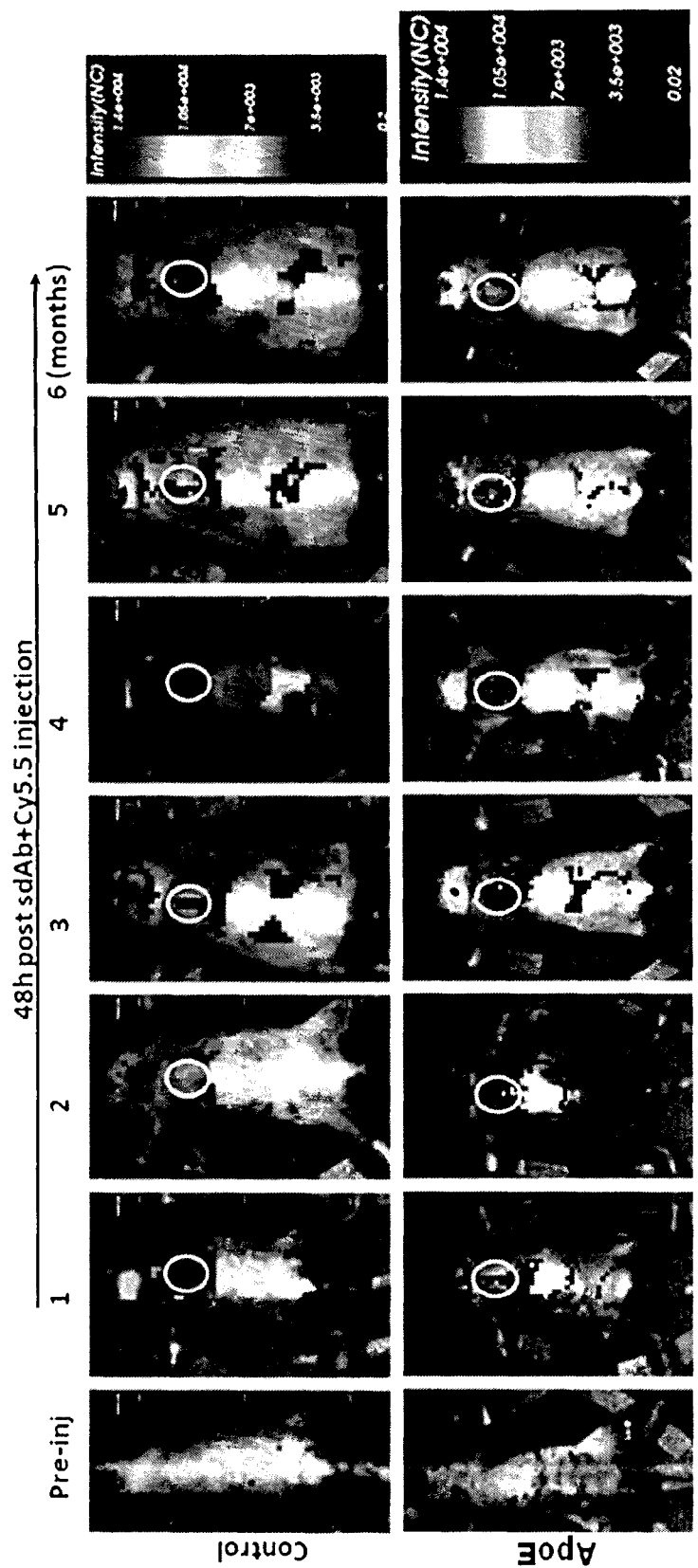
FIG. 23 is a visualization of atherosclerotic plaques using anti-ICAM 11-4 sdAb (gated fluorescence lifetime 1.85-1.95 ns), compared between control mice and ApoE −/− mice. The heart/aortic region (circled) of ApoE −/− mice has a progressive increase in fluorescent signal indicative of increased atheroscleroic plaques. In contrast, control mice have low fluorescent signal in the heart/aortic region. This shows that the anti-ICAM-1 sdAb has the ability to detect atherosclerotic plaques and that fluorescent lifetime gating can increase accuracy (specificity) of detection.

Lifetime gating analyses were performed to analyse differences in Cy5.5 signal observed in the heart, liver and bladder. This method selectively displays only the specific lifetime values. Briefly, the fluorescence decay was estimated using eXplore Optix OptiView software. The software deconvoluted the measured fluorescent intensity-time decay curve using Levenberg-Marquardt Algorithm, which applies a non-linear least-squares minimization algorithm to compute the coefficients of a multi-exponential expansion of the fluorescence decay. Unbound deactivated Cy5.5 dye has a lifetime value of 1.0 to 1.3 ns, while the conjugated anti-ICAM-1 sdAb-Cy5.5 shows a value of approximately 1.9 ns. Using the fluorescence lifetime analyses and gating for specific fluorescence lifetime spans, the lifetime value of the signal in each region of interest was determined. Lifetime gating of 1.05-1.65 ns resulted in a signal predominantly in the bladder (FIGS. 19 and 20); 1.05-1.85 ns showed a signal predominantly in the liver region (data not shown), which can be attributed to a mixture of anti-ICAM-1 sdAb-Cy5.5 and free Cy5.5 fluorophore due to metabolism; and 1.85 ns-1.95 ns predominantly showed anti-ICAM-1 sdAb bound to plaques in the heart/aortic region (FIGS. 21 and 22). Thus, gating for fluorescent lifetime (1.85-1.95 ns) showed that the bound anti-ICAM-1 sdAb-Cy5.5 is found only in the heart/aortic region in ApoE knockout animals, while the specific anti-ICAM-1sdAb-Cy5.5 signal was not detected the same region of control animals (FIG. 23)

Overall, the results confirm the ability of anti-ICAM-1 sdAb to selectively bind to ICAM-1 receptor in vivo after intravenous injection; they also demonstrate the ability of anti-ICAM-1 sdAb to differentiate between inflamed plaques in ApoE KO mice and control mice.

EXAMPLE 8

Ex-Vivo Imaging of Aortic Sections from ApoE KO and C578 Control Mice

Hearts and aortas from the mice of Example 7 were dissected and imaged ex vivo in eXplore Optix.

Figure 24A:
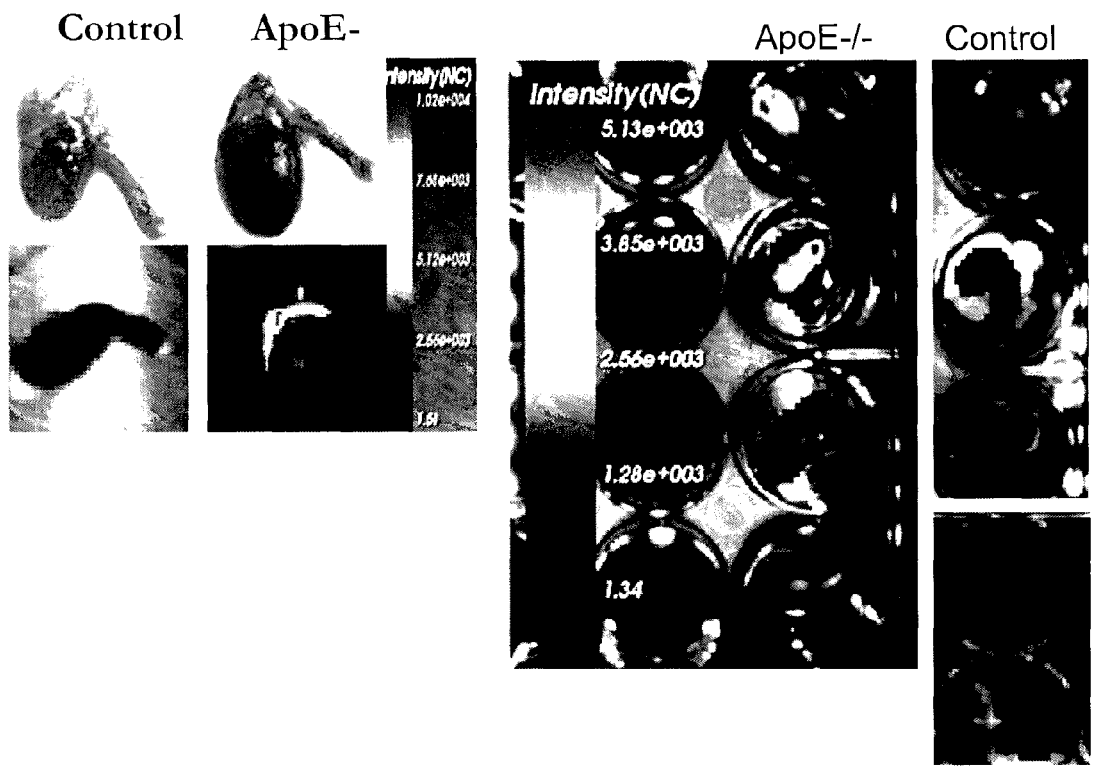
FIG. 24 shows results of ex vivo imaging (FIG. 24A) and quantification (FIG. 24B) of the optical signal in isolated heart and thoracic aorta of ApoE KO and control mice 6 months after start of high-fat diet. The mice were injected with 50 μg of anti-ICAM-1 sdAb 11-4 labelled with Cy5.5 and sacrificed 48 h after injection. Hearts and aortas were excised and imaged ex vivo. The results show significantly higher fluorescence signal in heart/aorta of APOE KO mice compared to control mice.
Figure 24B:
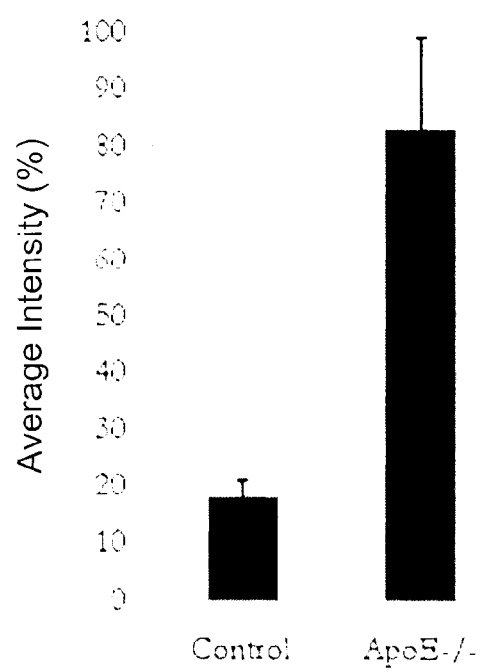
Figure 25:
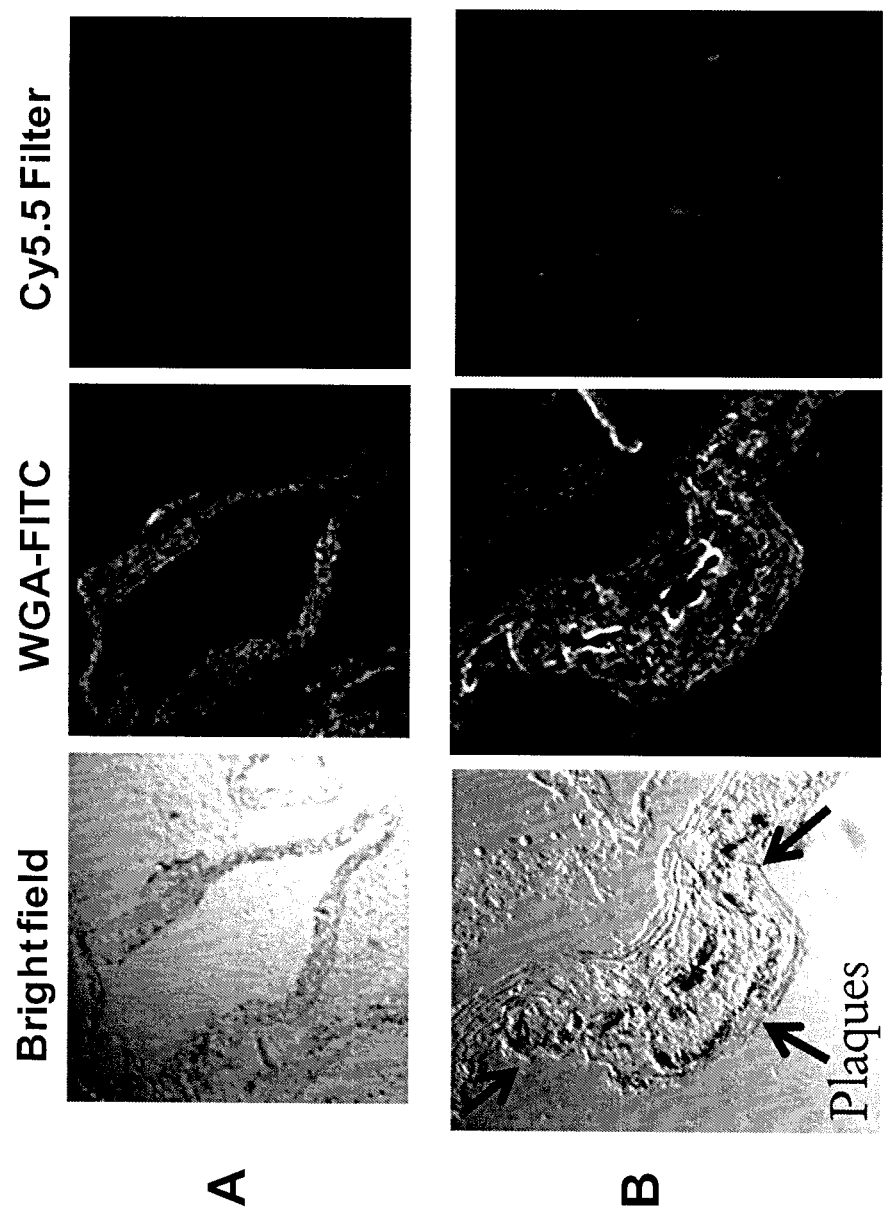
FIG. 25 shows fluorescently stained frozen sections images of aortas of control C57Bl/6 (upper panels, A) and ApoE KO (lower panels, B) injected with 50 μg anti-ICAM-1 sdAb 11-4 labelled with Cy5.5 at 6 months of high fat diet. Mice were sacrificed 48 h after sdAb injection. Hearts and aortas were excised and sectioned. Fluorescence microscopy data indicates that intravenously injected anti-ICAM-1 sdAb 11-4-

Results are shown in FIG. 24. Optical analysis of the signal obtained from ex vivo imaging (FIG. 24) revealed that ICAM-1 signal was localized mainly to the aortic root as well as to the aortic arch. FIG. 24A shows that the fluorescence intensity signal was higher in dissected hearts/aortas from ApoE-knockout animals than in control animals (from Example 6). FIG. 24B is a graph showing quantitation of images in FIG. 24A. Average signal intensity from dissected hearts/aortas from ApoE knockout animals was 3-fold higher than that from control animals.

Aortas imaged ex vivo were then frozen, sectioned and processed for fluorescent microscopy. Cy5.5 signal of injected anti-ICAM-1 sdAb is visualized under microscope using appropriate filters (ex 665/45, em 725/50, beamsplitter FT 695). Data shown in FIG. 25 indicates that the injected anti-ICAM sdAb-Cy5.5 (red) co-localized with atherosclerotic plaques in frozen aorta sections in ApoE KO mice. No ICAM-1 signal (red) was observed in aorta sections from control mice injected with anti-ICAM sdAb-Cy5.5.

EXAMPLE 9

Monitoring Therapy of Carotid Atherosclerosis Using Anti-ICAM-1 sdAb

The anti-ICAM-1 single domain antibody clone 11-4 (Example 4) was used as a surrogate biomarker for monitoring therapy of carotid atherosclerosis. The protocol for the study is shown in FIG. 26.

ApoE KO and age-matched C57Bl/6 WT mice after 4 months of high fat diet, as described in Example 6, were divided into two groups; for 2 months, one group was fed their regular diet while the other group received 25 mg/Kg/day of the cholesterol-lowering drug Atorvastatin (Lipitor) in their food. Animals in each of the 4 groups were then administered anti-ICAM-1 sdAb (50 ug) labelled with Cy5.5 and were imaged non-invasively in eXplore Optix near-infrared optical imager.

Results are shown in FIG. 27, which indicates that imaging using anti-ICAM-1 sdAb can demonstrate the reduction of inflammation in atherosclerotic plaques (ICAM-1 expression) following Atorvastatin treatment.

EXAMPLE 10

Molecular Imaging of Brain Vascular/Endothelial Pro-Inflammatory Activation in Stroke Using ICAM-1 sdAb The endothelial adhesion molecule, ICAM-1, is expressed on luminal surface of brain vessels and is robustly up-regulated in different brain diseases, including stroke and multiple sclerosis. ICAM-1 is associated with leukocyte infiltration into the brain after ischemia. The clinical need for assessing and eventually therapeutically modulating endothelial inflammatory activation following stroke is still unmet. Developing a molecular imaging agent which can detect ICAM-1 expression in the brain vessels after stroke can aid in selecting approaches to manage stroke (e.g., anti-inflammatory agents to treat brain inflammation).

All procedures using animals were approved by the institutional Animal Care Committee and comply with the guidelines established by the Canadian Council on Animal Care. Male CD-1 mice (23-25 g) were obtained from Charles River and bred locally. Anesthesia was induced with 1.5% isoflurane and maintained with 1.0% isoflurane in 69% $N_2O$ and 30% $O_2$ using a vaporizer. Mice were subjected to occlusion of the left middle cerebral artery (MCA) using an intraluminal filament. Briefly, an 11-mm silicone-coated nylon thread was introduced into the left common carotid artery of an anesthetized mouse and directed into the internal carotid artery until it obstructed blood flow to the MCA for 1 hour. Sham-operated mice, which were subjected to the same brain surgery but no MCAO, were used as controls.

The up-regulation of ICAM-1 expression in brain vessels after stroke was evaluated using immunofluorescence approaches. Vessels were detected in brain sections using fluorescently-labeled Tomato lectin (green), and ICAM-1 expression was detected using monoclonal anti-ICAM-1 antibody followed with secondary antibody. FIG. 28 shows ICAM-1 expression in virtually all brain vessels after stroke compared to occasional vessel expressing ICAM-1 in sham-operated animals.

Mice subjected to permanent MCAO for 1 hour or sham-operated animals were injected in the tail vein with 50 microgram of anti-ICAM-1 sdAb labeled with Cy5.5 fluorophore and then imaged at 3 h, 5 h, and 6 h post-injection with time-domain optical imager MX2.

After imaging, animals were perfused with heparinized saline and 10% formalin, and sectioned using vibrotome into 25 micron thick sections. Sections were histochemically stained with the Tomato Lectin-FITC (1:100; 30 min) to identify brain vessels. The anti-ICAM-1 sdAb signal was assessed by visualizing Cy5.5 in brain using a Zeiss Axiovert 200 fluorescent microscope (Carl Zeiss, Maple Groove, Minn., USA) in a near-infrared mode (a 660- to 680-nm excitation filter and a 700-nm longpass emission filter).

FIG. 29 shows high and persistent fluorescence signal in the right side of the head ROI in animals subjected to permanent MCAO and injected with anti-ICAM-1 sdAb-Cy5.5. This indicates a) that the fluorescent probe does not reach left side of the brain where circulation was blocked by MCAO, and that it produces high signal in the rest of the brain indicative of high ICAM-1 expression in brain vessels after stroke shown in FIG. 28. FIG. 30 confirms the in vivo imaging observations shown in FIG. 29, in that in the brains imaged ex-vivo fluorescent signal from anti-ICAM-1sdAb-Cy5.5 probe is localized in the brain regions not affected by infarct (induced on the left side)).

To confirm the results and provide anatomical information on the ICAM-1 signal observed by optical fluorescence imaging, co-registration of optical imaging and microcomputed tomography of brain vessels was performed. To visualize the brain vessels and obtain anatomical information of the location of the signal originating from anti-ICAM-1 sdAb injection after MCAO, Microfil-enhanced X-ray micro-computed tomography was performed. Briefly, Micro-CT images were obtained by sacrificing mice with permanent MCAO and injected with anti-ICAM-1 sdAb for 6 hours, by intra cardiac perfusion of the blood with heparinized saline, followed by infusing a radiopaque silicone polymer as a blood pool contrast agent (Microfil MV-122, Flow Tech, Carver, Mass.), which was left to polymerize over-night, followed by fixing in 10% formalin. In preparation for scanning with micro-CT, the brains were removed from the skulls and mounted in 1% agar. Each image was acquired over 900 projection views through 360° rotation and three-dimensional CT images were reconstructed with $27 \times 27 \times 27$-$\mu m^3$ voxels using a GE eXplore Locus Scanner (GE Healthcare Biosciences, London, ON) at 27 µm isotropic resolution. To co-Register injected ICAM-1-cy5.5 (optical imaging) and microfil perfused brain (microCT imaging), CT-Fusion volume was generated with the OptiView™ CT-Fusion software module (ART, Advanced Research Technologies Inc.) and exported in DICOM format for co-registration using AMIRA®, a 3D biomedical visualization software analysis tool from Visage Imaging™ (San Diego, Calif.). The co-registration technique employed by OptiView™ matches the X-ray fiducial markers that appear on microCT images with software markers that are inserted at pre-determined positions into the optical image volume slices. AMIRA® software was then used to co-register and visualize the optical and CT images.

FIG. 31 shows reconstructed co-registered image of molecular optical signal (originating from injected ICAM-1sdAb-Cy5.5) and the brain vascular bed in the same animal imaged by microCT after perfusion with microfilm. The image shows lack of perfusion on the left side of the brain (where MCA was occluded) and intact vascular bed on the right side of the brain. The optical signal, indicating region of ICAM-1 expression is localized in the right side of the brain.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein are hereby incorporated by reference.

Arbabi Ghahroudi M, Desmyter A, Wyns L, Hamers R, Muyldermans S. Selection and identification of single domain antibody fragments from camel heavy-chain antibodies. FEBS Lett. 1997; 414:521-6.

Arbabi-Ghahroudi M, MacKenzie R, Tanha J. Selection of non-aggregating VH binders from synthetic VH phage-display libraries. Methods Mol Biol. 2009; 525:187-216, xiii.

Bell A, Wang Z J, Arbabi-Ghahroudi M, Chang T A, Durocher Y, Trojahn U, Baardsnes J, Jaramillo M L, Li S, Baral T N, O'Connor-McCourt M, Mackenzie R, Zhang J. Differential tumor-targeting abilities of three single-domain antibody formats. Cancer Lett. 2010; 289:81-90.

Chothia C, Lesk A M. Canonical structures for the hypervariable regions of immunoglobulins. J Mol Biol. 1987; 196(4):901-17.

de Kruif, J. & Logtenberg, T. Leucine zipper dimerized bivalent and bispecific scFv antibodies from a semi-synthetic antibody phage display library. J Biol Chem 271, 7630-7634 (1996).

Dougherty G. J., Murdoch S., and Hogg N. The function of human intercellular adhesion molecule-1 (ICAM-1) in the generation of an immune response. Eur J Immunol 1988: 18, 35-39.

Doyle P J, Arbabi-Ghahroudi M, Gaudette N, Furzer G, Savard M E, Gleddie S, McLean M D, Mackenzie C R, Hall J C. Cloning, expression, and characterization of a single-domain antibody fragment with affinity for 15-acetyl-deoxynivalenol. Mol Immunol. 2008; 45:3703-13.

Eisenberg, D.; E. Schwarz; M. Komaromy & R. Wall (1984) Analysis of membrane and surface protein sequences with the hydrophobic moment plot. J Mol Biol, 179, 125-142

Hamers-Casterman, C. et al. Naturally occurring antibodies devoid of light chains. Nature 363, 446-448 (1993).

Iiyama K, Hajra L, Iiyama M, Li H, DiChiara M, Medoff B D, Cybulsky M I (1999), Patterns of vascular cell adhesion molecule-1 and intercellular adhesion molecule-1 expression in rabbit and mouse atherosclerotic lesions and at sites predisposed to lesion formation. Circ Res 1999;85:199-207.

Iqbal U, Trojahn U, Albaghdadi H, Zhang J, O'Connor M, Stanimirovic D, Tomanek B, Sutherland G, Abulrob A (2010) Kinetic analysis of novel mono- and multivalent VHH-fragments and their application for molecular targeting of brain tumors. British Journal of Pharmacology (in press)

Jaff M R, Goldmakher G V, Lev M H, Romero J M. Imaging of the carotid arteries: the role of duplex ultrasonography, magnetic resonance arteriography, and computerized tomographic arteriography. Vasc Med. 2008 November; 13(4):281-92.

Jespers, L., Schon, O., Famm, K. & Winter, G. Aggregation-resistant domain antibodies selected on phage by heat denaturation. Nat Biotechnol 22, 1161-1165 (2004).

Kabat E A, Wu T T. Identical V region amino acid sequences and segments of sequences in antibodies of different specificities. Relative contributions of VH and VL genes, mini-genes, and complementarity-determining regions to binding of antibody-combining sites. J Immunol. 1991; 147: 1709-19.

Kitagawa K, Matsumoto M, Sasaki T, Hashimoto H, Kuwabara K, Ohtsuki T, Hori M (2002), Involvement of ICAM-1 in the progression of atherosclerosis in APOE-knockout mice, Atherosclerosis 160: 305-310.

Merritt, E. A. & Hol, W. G. AB5 toxins. *Current opinion in structural biology* 5, 165-171 (1995).

Nakashima Y, Raines E W, Plump A S, Breslow J L, Ross R. Upregulation of VCAM-1 and ICAM-1 at atherosclerosis-prone sites on the endothelium in the ApoE-deficient mouse. Arterioscler Thromb Vasc Biol. 1998:18:842-51.

Nielsen, U. B., Adams, G. P., Weiner, L. M. & Marks, J. D. Targeting of bivalent anti-ErbB2 diabody antibody fragments to tumor cells is independent of the intrinsic antibody affinity. Cancer research 60, 6434-6440 (2000).

Nuttall, S. D. et al. Isolation and characterization of an IgNAR variable domain specific for the human mitochondrial translocase receptor Tom70. European journal of biochemistry/FEBS 270, 3543-3554 (2003).

Padlan, E. A. Anatomy of the antibody molecule. Molecular immunology 31, 169-217 (1994).

Ridgway, J. B., Presta, L. G. & Carter, P. 'Knobs-into-holes' engineering of antibody CH3 domains for heavy chain heterodimerization. Protein Eng 9, 617-621 (1996).

Sadat U, Li Z Y, Graves M J, Tang T Y, Gillard J H. Noninvasive imaging of atheromatous carotid plaques. Nat Clin Pract Cardiovasc Med. 2009 March; 6(3):200-9.

Tanha J, Muruganandam A, Stanimirovic D. Phage display technology for identifying specific antigens on brain endothelial cells. Methods Mol Med. 2003; 89:435-49.

Tanha J, Xu P, Chen Z, Ni F, Kaplan H, Narang S A, MacKenzie C R. Optimal design features of camelized human single-domain antibody libraries. J Biol Chem. 2001 Jul. 6; 276(27):24774-80.

To, R. et al. Isolation of monomeric human V(H)s by a phage selection. J Biol Chem 280, 41395-41403 (2005).

Zhang, J. et al. A pentavalent single-domain antibody approach to tumor antigen discovery and the development of novel proteomics reagents. *J Mol Biol* 341, 161-169 (2004).

Zhang, J. et al. Pentamerization of single-domain antibodies from phage libraries: a novel strategy for the rapid generation of high-avidity antibody reagents. *J Mol Biol* 335, 49-56 (2004).

International PCT Publication No. WO2003/046560

The invention claimed is:

1. An isolated or purified antibody or fragment thereof that specifically binds to intercellular adhesion molecule 1 (ICAM-1), comprising
the sequence of complementarity determining region (CDR) 1 selected from sequences LYVMG (SEQ ID NO:1), AFRMG (SEQ ID NO:2), and INDMG (SEQ ID NO:3);
the sequence of CDR2 selected from sequences DITSSGSIYYVDSLKG (SEQ ID NO:4), VITAGGTTSYIDSVKG (SEQ ID NO:5), and RITRDGSAAYEDSVKG (SEQ ID NO:6); and
the sequence of CDR3 selected from sequences HVRQDSGSEYLTY (SEQ ID NO:7), IDYDS (SEQ ID NO:8), and EIITTQTLGRMLGEY (SEQ ID NO:9).

2. The isolated or purified antibody or fragment thereof of claim 1, comprising a CDR1 of sequence LYVMG (SEQ ID NO:1), a CDR2 of sequence DITSSGSIYYVDSLKG (SEQ ID NO:4), and a CDR3 of sequence HVRQDSGSEYLTY (SEQ ID NO:7).

3. The isolated or purified antibody or fragment thereof of claim 1, comprising a CDR1 of sequence AFRMG (SEQ ID NO:2), a CDR2 of sequence VITAGGTTSYIDSVKG (SEQ ID NO:5), and a CDR3 of sequence IDYDS (SEQ ID NO:8).

4. The isolated or purified antibody or fragment thereof of claim 1, comprising a CDR1 of sequence INDMG (SEQ ID NO:3), a CDR2 of sequence RITRDGSAAYEDSVKG (SEQ ID NO:6), and a CDR3 of sequence EIITTQTLGRMLGEY (SEQ ID NO:9).

5. The isolated or purified antibody or fragment thereof of claim 1, wherein the isolated or purified antibody or fragment thereof is a single-domain antibody (sdAb).

6. The isolated or purified antibody or fragment thereof of claim 5, wherein the sdAb is of camelid origin.

7. The isolated or purified antibody or fragment thereof of claim 1 comprising the sequence:

```
(SEQ ID NO: 10)
QVQLVESGGGLVQPGGSLRLSCAASGSISSLYVMGWYRQAPGKQRELV

ADITSSGSIYYVDSLKGRFTISRDNARSTVYLQMNSLEPEDTAVYYCM

AHVRQDSGSEYLTYWGQGTQVTVSS, (SEQ ID NO: 11)
QVKLEESGGGLVQAGDSLRLSCAASGRTVNAFRMGWYRQAPGKQRERV

AVITAGGTTSYIDSVKGRFTISRDNAKNTVYLQMNSLKPEDTAVYYCA

AIDYDSRGQGTQVTVSS,
or (SEQ ID NO: 12)
QVKLEESGGGLVQPGGSLRLSCAASGSIFSINDMGWYRQAPGKQRELV

ARITRDGSAAYEDSVKGRFTISRDNAPNTVFLQMNGLKPEDTAVYYCN

AEIITTQTLGRMLGEYWGQGTQVTVSS.
```

8. A targeted therapeutic agent comprising the isolated or purified antibody or fragment thereof of claim 1 linked to a therapeutic.

9. The targeted therapeutic agent of claim 8, wherein the therapeutic agent treats conditions selected from the group consisting of carotid artery disease, stroke, myocardial infarction, inflammatory bowel disease, autoimmune diseases, multiple sclerosis, Crohn's disease, and neovascularization associated with tumour angiogenesis.

10. A molecular imaging agent comprising the isolated or purified antibody or fragment thereof of claim 1 linked to a detectable agent.

11. The molecular imaging agent of claim 10, wherein the detectable agent is selected from the group consisting of a radioisotope, a paramagnetic label, a fluorophore, an echogenic microbubble, an affinity label, and an enzyme.

12. The molecular imaging agent of claim 10, wherein the detectable agent is a near infrared fluorescence (NIRF) imaging dye.

13. An ex vivo method of detecting atherosclerotic plaques, comprising:
a) providing a tissue sample suspected of inflammation and plaque formation;
b) contacting said sample with the isolated or purified antibody or fragment thereof of claim 1 under suitable conditions; and
c) detecting the formation of a protein complex,
wherein the isolated or purified anti-ICAM-1 antibody or fragment thereof binds to the tissue sample comprising atherosclerotic plaque formation at a higher rate than that of a control sample.

14. The ex vivo method of claim 13, wherein the step of detecting (step c)) is accomplished by optical imaging, immunohistochemistry, molecular diagnostic imaging, or ELISA.

15. An in vivo method of detecting atherosclerotic plaques, comprising:
a) administering the molecular imaging agent of claim 10 to a subject;
b) allowing the molecular imaging agent to bind to ICAM-1, wherein the molecular imaging agent binds to binds ICAM-1 in atherosclerotic plagues in vivo at a detectably higher rate than the rate of binding to normal vasculature; and
c) detecting the binding of the molecular imaging agent, wherein the binding of said molecular imaging agent to the vasculature is indicative of the presence of atherosclerotic plaques.

16. The in vivo method of claim 15, wherein the step of detecting (step b)) is accomplished by non-invasive optical imaging, ultrasound, MRI, PET, or SPECT.

17. A method for detecting ICAM-1 overexpression in a patient, said method comprising administering an effective amount of the molecular imaging agent of claim 10 to the patient and detecting ICAM-1 bound to the imaging agent.

18. The method of claim 17, wherein the patient has vascular inflammation, stroke, cancer, or angiogenesis.

19. The method of claim 17, wherein the step of detecting is accomplished by non-invasive optical imaging, ultrasound, MRI, PET, or SPECT.

* * * * *